United States Patent [19]

Loewe et al.

[11] 4,010,272

[45] Mar. 1, 1977

[54] ANTHELMINTICALLY ACTIVE BASICALLY SUBSTITUTED 2-CARBALKOXY-AMINO-BENZIMIDAZO-LYL-5(6)-PHENYL ETHERS AND -KETONES

[75] Inventors: Heinz Loewe, Kelkheim, Taunus; Josef Urbanietz, Schwalbach, Taunus; Dieter Düwel, Hofheim, Taunus; Reinhard Kirsch, Niederjosbach, Taunus, all of Germany

[73] Assignee: Hoechst Aktiengesellschaft, Frankfurt am Main, Germany

[22] Filed: Sept. 8, 1975

[21] Appl. No.: 611,325

[30] Foreign Application Priority Data

Sept. 10, 1974 Germany .......................... 2443297

[52] U.S. Cl. ............................ 424/273; 260/243 B; 260/247.1 R; 260/247.1 L; 260/247.2 A; 260/247.5 R; 260/293.6; 260/293.73; 260/293.79; 260/326.5 R; 260/326.5 S; 260/570.7; 260/571; 260/309.2

[51] Int. Cl.² ........................................ C07D 235/32

[58] Field of Search ...... 260/309.2, 293.6, 247.1 L, 260/247.2 A, 243 B; 424/273, 267, 248, 246

[56] References Cited

UNITED STATES PATENTS

| 3,657,267 | 4/1972 | Van Gelder et al. | 260/309.2 |
|---|---|---|---|
| 3,904,621 | 9/1975 | Rochling et al. | 260/293.6 |
| 3,928,375 | 12/1975 | Düwel et al. | 260/309.2 |

FOREIGN PATENTS OR APPLICATIONS

| 2,048,150 | 3/1971 | France | 260/309.2 |
|---|---|---|---|
| 2,071,334 | 9/1971 | France | 260/309.2 |

*Primary Examiner*—Natalie Trousof
*Attorney, Agent, or Firm*—Curtis, Morris & Safford

[57] ABSTRACT

Anthelmintically active basically substituted 2-carbalkoxy-amino-benzimidazolyl-5(6)-phenyl ethers and -ketones are disclosed as well as a process for preparing them. The compounds are chemotherapeutics having a particular activity against ankylostomes, other helminths as well as liver fluke.

12 Claims, No Drawings

ANTHELMINTICALLY ACTIVE BASICALLY SUBSTITUTED 2-CARBALKOXY-AMINO-BENZIMIDAZOLYL-5(6)-PHENYL ETHERS AND -KETONES

2-Carbalkoxyamino-benzimidazole derivatives with alkyl, acyl, phenoxy and phenylthio radicals in 5(6)-position are known as anthelmintics (P. Actor u.a. Nature 215, 321 (1967); German Offenlegungsschrift No. 2,029,637; German Offenlegungsschrift No. 2,164,690), The present invention relates to anthelmintically active basically substituted 2-carbalkoxyamino-benzimidazolyl-5-(6-phenyl ethers and -ketones of the formula (1)

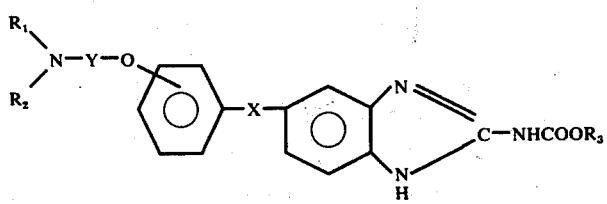

(1)

wherein $R_3$ is alkyl having 1 to 4 carbon atoms, X is oxygen, sulfur or

Y is a straight-chained or branched alkylene group having 1 to 4 carbon atoms and $R_1$ and $R_2$ represent an alkyl radical having 1 to 4 carbon atoms, whereby the two radicals $R_1$ and $R_2$ together with the supporting nitrogen atom may also represent the pyrrolidine, piperidine, morpholine or thiomorpholine ring.

As alkyl radicals in the substituents $R_1$, $R_2$ and $R_3$ there are especially considered methyl, ethyl, propyl, isopropyl, butyl, secundary butyl and tertiary butyl. As alkylene group Y there are especially considered the ethylene, propylene, butylene, methylethylene, methylpropylene and dimethylethylene group.

The invention further relates to a process for preparing basically substituted 2-carbalkoxyamino-benzimidazolyl-5-(6)-phenyl ethers and -ketones of the formula (1), wherein $R_1$, $R_2$, $R_3$, X and Y have the above meanings, which comprises condensing an o-phenylene-diamino derivative of the formula (2)

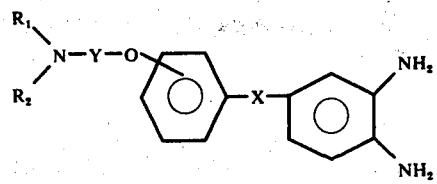

(2)

wherein $R_1$, $R_2$, X and Y have the same meanings as in formula (1), a. with an alkyl-S-methyl-thio-urea-carboxylate of the formula (3)

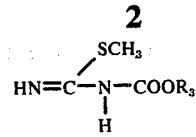

(3)

wherein $R_3$ has the same meaning as in formula (1), or b. with a cyanaide carboxylate or the formula (4)

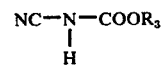

(4)

wherein $R_3$ has the same meaning as in formula (1), in each case in a pH-range of from 1 to 6, preferably 2 to 5, or c. reacting with a bis-alkyl- or bis-arylthio-methylene-amino-formic acid ester of the formula (5)

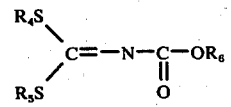

(5)

wherein $R_6$ has the meaning given for $R_3$ in formula (1) and $R_4$ and $R_5$ are identical or different from each other and represent an alkyl radical having 1 to 4 carbon atoms, an alkenyl radical having 3 to 5 carbon atoms, a cyclohexyl radical or an optionally substituted phenyl or benzyl radical of the formula (6) or (7)

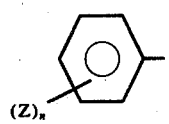 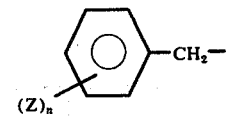

wherein Z represents independently from one another halogen, methyl or nitro, or in which $R_4$ and $R_5$ may also be closed to a ring containing 2 or 3 methylene groups, and wherein n represents the integer 0, 1 or 2. The 2-carbalkoxyamino-benzimidazolyl-5-(6)-phenyl ethers of the formula (1), may, if desired, be converted into the corresponding salt by addition of a physiologically tolerable acid; as acids there are suitable inorganic acids, as for example hydrochloric acid, sulfuric acid, phosphoric acid or organic acids, as for example acetic acid, lactic acid, aceturic acid, succinic acid, tartric acid, glucuronic acid or citric acid.

A particularly good activity is possessed by the compounds of the formula (1) in which $R_1$ and $R_2$ represent methyl/or ethyl or form the piperidine ring together with the nitrogen atom carrying them, Y represents $-(CH_2)_2-$ or $-(CH_2)_3-$ and $R_3$ is methyl, whereas X is oxygen, sulfur or a $\diagdown$C=O group.

The development of the reactions may be illustrated by the following scheme

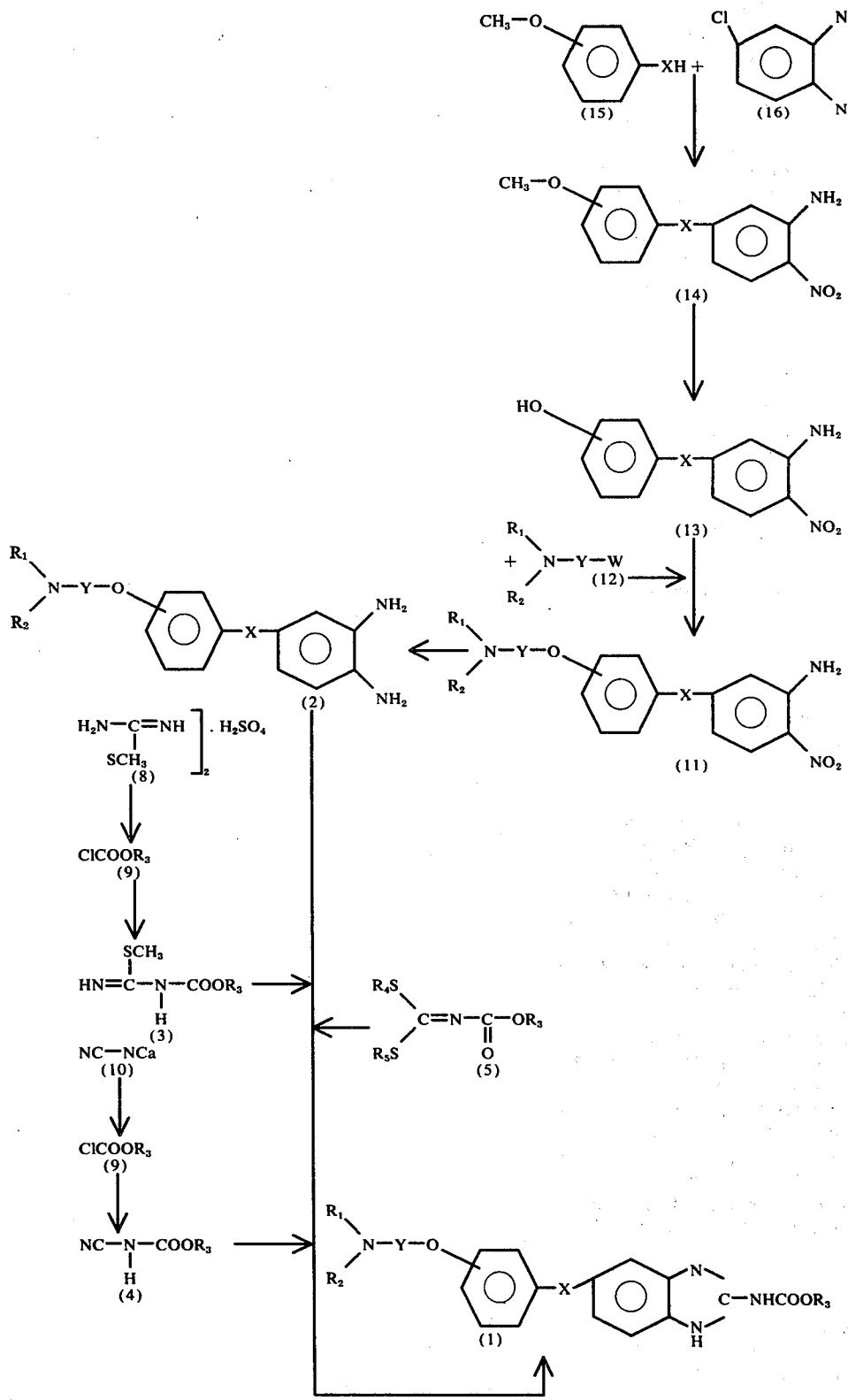

To carry out the reaction according to a) the S-methyl-thio-urea-sulfate of the formula (8) and a chloroformic acid ester of the formula (9), wherein $R_3$ has the same meaning as in formula (1), in water, a strong base is added dropwise, for example a 25% sodium hydroxide solution, the temperature being maintained at a low degree, preferably about 0° C. The alkyl-S-methyl-thio-urea-carboxylate formed of the formula (3) need not be isolated.

As chloroformic acid ester of the formula (9) there are
considered for example the chloroformic acid methyl ester
chloroformic acid ethyl ester
chloroformic acid propyl ester
chloroformic acid isopropyl ester
chloroformic acid butyl ester
chloroformic acid isobutyl ester
chloroformic acid tertiary butyl ester.

The pH-range of the preparation obtained as described above is preferably adjusted to a value of from 2 and 5, expediently by addition of an organic acid such as acetic acid or lactic acid. Then the o-phenylene-diamino derivative of the formula (2) is added, either as a free base or as an acid addition salt, for example as hydrochloride. In the latter case it may be advantageous to add an alkali salt or an organic acid as buffer.

As o-phenylene-diamino derivatives of the formula (2) there are considered for example the 4-[4-(2-Dimethylamino-ethoxy)-phenoxy]-2-amino-aniline
4-[4-(3-Dimethylamino-ethoxy)-phenoxy]-2-amino-aniline
4-[4-(4-Dimethylamino-butoxy)-phenoxy]-2-amino-aniline
4-[4-(2-Dimethylamino-1-methyl-ethoxy)-phenoxy]-2-amino-aniline
4-[4-(2-Dimethylamino-2-methyl-ethoxy)-phenoxy]-2-amino-aniline
4-[4-(2-Dimethylamino-1,2-dimethyl-ethoxy)-phenoxy]-2-amino-aniline
4-[4-(2-Diethylamino-ethoxy)-phenoxy]-2-amino-aniline
4-[4-(3-Diethylamino-propoxy)-phenoxy]-2-amino-aniline
4-[4-(4-Diethylamino-butoxy)-phenoxy]-2-amino-aniline
4-[4-(2-Diethylamino-1-methyl-ethoxy)-phenoxy]-2-amino-aniline
4-[4-(2-Diethylamino-2-methyl-ethoxy)-phenoxy]-2-amino-aniline
4-[4-(2-Diethylamino-1,2-dimethyl-ethoxy)-phenoxy]-2-amino-aniline
4-[4-(2-Dipropylamino-ethoxy)-phenoxy]-2-amino-aniline
4-[4-(3-Dipropylamino-propoxy)-phenoxy]-2-amino-aniline
4-[4-(4-Dipropylamino-butoxy)-phenoxy]-2-amino-aniline
4-[4-(2-Dipropylamino-1-methyl-ethoxy)-phenoxy]-2-amino-aniline
4-[4-(2-Dipropylamino-2-methyl-ethoxy)-phenoxy]-2-amino-aniline
4-[4-(2-Dipripylamino-1,2-dimethyl-ethoxy)-phenoxy]-2-amino-aniline
4-[4-(2-Diisopropylamino-ethoxy)-phenoxy]-2-amino-aniline
4-[4-(3-Diisopropylamino-propoxy)-phenoxy]-2-amino-aniline
4-[4-(4-Diisopropylamino-butoxy)-phenoxy]-2-amino-aniline
4-[4-(2-Diisopropylamino-1-methyl-ethoxy)-phenoxy]-2-amino-aniline
4-[4-(2-Diisopropylamino-2-methyl-ethoxy)-phenoxy]-2-amino-aniline
4-[4-(2-Diisopropylamino-1,2-dimethyl-ethoxy)-phenoxy]-2-amino-aniline
4-[4-(2-Dibutylamino-ethoxy)-phenoxy]-2-amino-aniline
4-[4-(3-Dibutylamino-propoxy)-phenoxy]-2-amino-aniline
4-[4-(4-Dibutylamino-butoxy)-phenoxy]-2-amino-aniline
4-[4-(2-Dibutylamino-1-methyl-ethoxy)-phenoxy]-2-amino-aniline
4-[4-(2-Dibutylamino-2-methyl-ethoxy)-phenoxy]-2-amino-aniline
4-[4-(2-Dibutylamino-1,2-dimethyl-ethoxy)-phenoxy]-2-amino-aniline
4-[4-(2-Pyrrolidyl-ethoxy)-phenoxy]-2-amino-aniline
4-[4-(3-Pyrrolidyl-propoxy)-phenoxy]-2-amino-aniline
4-[4-(4-Pyrrolidyl-butoxy)-phenoxy]-2-amino-aniline
4-[4-(Pyrrolidyl-1-methyl-ethoxy)-phenoxy]-2-amino-aniline
4-[4-(2-Pyrrolidyl-2-methyl-ethoxy)-phenoxy]-2-amino-aniline
4-[4-(2-Pyrrolidyl-1,2-dimethyl-ethoxy)-phenoxy]-2-amino-aniline
4-[4-(2-Piperidyl-ethoxy)-phenoxy]-2-amino-aniline
4-[4-(3-Piperidyl-propoxy)-phenoxy]-2-amino-aniline
4-[4-(4-Piperidyl-butoxy)-phenoxy]-2-amino-aniline
4-[4-(2-Piperidyl-1-methyl-ethoxy)-phenoxy]-2-amino-aniline
4-[4-(2-Piperidyl-2-methyl-ethoxy)-phenoxy]-2-amino-aniline
4-[4-(2-Piperidyl-1,2-dimethyl-ethoxy)-phenoxy]-2-amino-aniline
4-[4-(2-Morpholyl-ethoxy)-phenoxy]-2-amino-aniline
4-[4-(3-Morpholyl-propoxy)-phenoxy]-2-amino-aniline
4-[4-(4-Morpholyl-butoxy)-phenoxy]-2-amino-aniline
4-[4-(2-Morpholyl-1-methyl-ethoxy)-phenoxy]-2-amino-aniline
4-[4-(2-Morpholyl-2-methyl-ethoxy)-phenoxy]-2-amino-aniline
4-[4-(2-Morpholyl-1,2-dimethyl-ethoxy)-phenoxy]-2-amino-aniline
4-[3-(2-Dimethylamino-ethoxy)-phenoxy]-2-amino-aniline
4-[3-(3-Dimethylamino-propoxy)-phenoxy]-2-amino-aniline
4-[3-(4-Dimethylamino-butoxy)-phenoxy]-2-amino-aniline
4-[3-(2-Dimethylamino-1-methyl-ethoxy)-phenoxy]-2-amino-aniline
4-[3-(2-Dimethylamino-2-methyl-ethoxy)-phenoxy]-2-amino-aniline
4-[3-(2-Dimethylamino-1,2-dimethyl-ethoxy)-phenoxy]-2-amino-aniline
4-[3-(2-Dimethylamino-ethoxy)-phenoxy]-2-amino-aniline
4-[3-(3-Dimethylamino-propoxy)-phenoxy]-2-amino-aniline
4-[3-(4-Dimethylamino-butoxy)-phenoxy]-2-amino-aniline
4-[3-(2-Dimethylamino-1-methyl-ethoxy)-phenoxy]-2-amino-aniline
4-[3-(2-Dimethylamino-2-methyl-ethoxy)-phenoxy]-2-amino-aniline 4-[3-(2-Dimethylamino-1,2-dimethyl-ethoxy)-phenoxy]-2-amino-aniline
4-[3-(2-Dipropylamino-ethoxy)-phenoxy]-2-amino-aniline
4-[3-(3-Dipropylamino-propoxy)-phenoxy]-2-amino-aniline
4-[3-(4-Dipropylamino-butoxy)-phenoxy]-2-amino-aniline
4-[3-(2-Dipropylamino-1-methyl-ethoxy)-phenoxy]-2-amino-aniline
4-[3-(2-Dipropylamino-2-methyl-ethoxy)-phenoxy]-2-amino-aniline
4-[3-(2-Dipropylamino-1,2-dimethyl-ethoxy)-phenoxy]-2-amino-aniline
4-[3-Diisopropylamino-ethoxy)-phenoxy]-2-amino-aniline
4-[3-(3-Diisopropylamino-propoxy)-phenoxy]-2-amino-aniline
4-[3-(4-Diisopropylamino-butoxy)-phenoxy]-2-amino-aniline
4-[3-(2-Diisopropylamino-1-methyl-ethoxy)-phenoxy]-2-amino-aniline
4-[3-(2-Diisopropylamino-2-methyl-ethoxy)-phenoxy]-2-amino-aniline
4-[3-(2-Diisopropylamino-1,2-dimethyl-ethoxy)-phenoxy]-2-amino-aniline
4-[3-(2-Dibutylamino-ethoxy)-phenoxy]-2-amino-aniline
4-[3-(3-Dibutylamino-propoxy)-phenoxy]-2-amino aniline
4-[3-(4-Dibutylamino-butoxy)-phenoxy]-2-amino-aniline
4-[3-(2-Dibutylamino-1-methyl-ethoxy)-phenoxy]-2-amino-aniline
4-[3-(2-Dibutylamino-2-methyl-ethoxy)-phenoxy]-2-amino-aniline
4-[3-(2-Dibutylamino-1,2-dimethyl-ethoxy)-phenoxy]-2-amino-aniline
4-[3-(2-Pyrrolidyl-ethoxy)-phenoxy]-2-amino-aniline
4-[3-(3-Pyrrolidyl-propoxy)-phenoxy]-2-amino-aniline
4-[3-(4-Pyrrolidyl-butoxy)-phenoxy]-2-amino-aniline
4-[3-(2-Pyrrolidyl-1-methyl-ethoxy)-phenoxy]-2-amino-aniline
4-[3-(2-Pyrrolidyl-2-methyl-ethoxy)-phenoxy]-2-amino-aniline
4-[3-(2-Pyrrolidyl-1,2-dimethyl-ethoxy)-phenoxy]-2-amino-aniline
4-[3-Piperidyl-ethoxy)-phenoxy]-2-amino-aniline
4-[3-(3-Piperidyl-propoxy)-phenoxy]-2-amino-aniline
4-[3-(4-Piperidyl-butoxy)-phenoxy]-2-amino-aniline
4-[3-(2-Piperidyl-1-methyl-ethoxy)-phenoxy]-2-amino-aniline
4-[3-(2-Piperidyl-2-methyl-ethoxy)-phenoxy]-2-amino-aniline
4-[3-(2-Piperidyl-1,2-dimethyl-ethoxy)-phenoxy]-2-amino-aniline
4-[3-(2-Morpholyl-ethoxy)-phenoxy]-2-amino-aniline
4-[3-(3-Morpholyl-propoxy)-phenoxy]-2-amino-aniline
4-[3-(4-Morpholyl-butoxy)-phenoxy]-2-amino-aniline
4-[3-(2-Morpholyl-1-methyl-ethoxy)-phenoxy]-2-amino-aniline
4-[3-(2-Morpholyl-2-methyl-ethoxy)-phenoxy]-2-amino-aniline
4-[3-(2-Morpholyl-1,2-dimethyl-ethoxy)-phenoxy]-2-amino-aniline
4-[2-(2-Dimethylamino-ethoxy)-phenoxy]-2-amino-aniline
4-[2-(3-Dimethylamino-propoxy)-phenoxy]-2-amino-aniline
4-[2-(4-Dimethylamino-butoxy)-phenoxy]-2-amino-aniline
4-[2-(2-Dimethylamino-1-methyl-ethoxy)-phenoxy]-2-amino-aniline
4-[2-(2-Dimethylamino-2-methyl-ethoxy)-phenoxy]-2-amino-aniline
4-[2-(2-Dimethylamino-1,2-dimethyl-ethoxy)-phenoxy]-2-amino-aniline
4-[2-(2-Dimethylamino-ethoxy)-phenoxy]-2-amino-aniline
4-[2-(3-Dimethylamino-propoxy)-phenoxy]-2-amino-aniline
4-[2-(4-Dimethylamino-butoxy)-phenoxy]-2-amino-aniline
4-[2-(2-Dimethylamino-1-methyl-ethoxy)-phenoxy]-2-amino-aniline
4-[2-(2-Dimethylamino-2-methyl-ethoxy)-phenoxy]-2-amino-aniline
4-[2-(2-Dimethylamino-1,2-dimethyl-ethoxy)-phenoxy]-2-amino-aniline
4-[2-(2-Dipropylamino-ethoxy)-phenoxy]-2-amino-aniline
4-[2-(3-Dipropylamino-propoxy)-phenoxy[-2-amino-aniline
4-[2-(4-Dipropylamino-butoxy)-phenoxy]-2-amino-aniline
4-[2-(2-Dipropylamino-1-methyl-ethoxy)-phenoxy]-2-amino-aniline
4-[2-(2-Dipropylamino-2-methyl-ethoxy)-phenoxy]-2-amino-aniline
4-[2-(2-Dipropylamino-1,2-dimethyl-ethoxy)-phenoxy]-2-amino-aniline
4-[2-(2-Diisopropylamino-ethoxy)-phenoxy]-2-amino-aniline
4-[2-(3-Diisopropylamino-propoxy)-phenoxy]-2-amino-aniline
4-[2-(4-Diisopropylamino-butoxy)-phenoxy]-2-amino-aniline
4-[2-(2-Diisopropylamino-1-methyl-ethoxy)-phenoxy]-2-amino-aniline
4-[2-(2-Diisopropylamino-2-methyl-ethoxy)-phenoxy]-2-amino-aniline
4-[2-(2-Diisopropylamino-1,2-dimethyl-ethoxy)-phenoxy]-2-amino-aniline
4-[2-(2-Dibutylamino-ethoxy)-phenoxy]-2-amino-aniline
4-[2-(3-Dibutylamino-propoxy)-phenoxy[-2-amino-aniline
4-[2-(4-Dibutylamino-butoxy)-phenoxy]-2-amino-aniline
4-[2-(2-Dibutylamino-1-methyl-ethoxy)-phenoxy]-2-amino-aniline
4-[2-(2-Dibutylamino-2-methyl-ethoxy)-phenoxy]-2-amino-aniline
4-[2-(2-Dibutylamino-1,2-dimethyl-ethoxy)-phenoxy]-2-amino-aniline
4-[2-(2-Pyrrolidyl-ethoxy)-phenoxy]-2-amino-aniline
4-[2-(3-Pyrrolidyl-propoxy)-phenoxy]-2-amino-aniline
4-[2-(4-Pyrrolidyl-butoxy)-phenoxy]-2-amino-aniline
4-[2-(2-Pyrrolidyl-1-methyl-ethoxy)-phenoxy]-2-amino-aniline
4-[2-(2-Pyrrolidyl-2-methyl-ethoxy)-phenoxy]-2-amino-aniline
4-[2-(2-Pyrrolidyl-1,2-dimethyl-ethoxy)-phenoxy]-2-amino-aniline
4-[2-(2-Piperidyl-ethoxy)-phenoxy]-2-amino-aniline 4-[2-(3-Piperidyl-propoxy)-phenoxy]-2-amino-aniline
4-[2-(4-Piperidyl-butoxy)-phenoxy]-2-amino-aniline
4-[2-(2-Piperidyl-1-methyl-ethoxy)-phenoxy]-2-amino-aniline
4-[2-(2-Piperidyl-2-methyl-ethoxy)-phenoxy]-2-amino-aniline
4-[2-(2-Piperidyl-1,2-dimethyl-ethoxy)-phenoxy]-2-amino-aniline
4-[2-(2-Morpholyl-ethoxy)-phenoxy]-2-amino-aniline
4-[2-(3-Morpholyl-propoxy)-phenoxy]-2-amino-aniline
4-[2-(4-Morpholyl-butoxy)-phenoxy]-2-amino-aniline
4-[2-(2-Morpholyl-1-methyl-ethoxy)-phenoxy]-2-amino-aniline
4-[2-(2-Morpholyl-2-methyl-ethoxy)-phenoxy]-2-amino-aniline
4-[2-(2-Morpholyl-1,2-dimethyl-ethoxy)-phenoxy]-2-amino-aniline
4-[4-(2-Dimethylamino-ethoxy)-phenylthio]-2-amino-aniline
4-[4-(3-Dimethylamino-propoxy)-phenylthio]-2-amino-aniline
4-[4-(4-Dimethylamino-butoxy)-phenylthio]-2-amino-aniline
4-[4-(2-Dimethylamino-1-methyl-ethoxy)-phenylthio]-2-amino-aniline
4-[4-(2-Dimethylamino-2-methyl-ethoxy)-phenylthio]-2-amino-aniline
4-[4-(2-Dimethylamino-1,2-dimethyl-ethoxy)-phenylthio]-2-amino-aniline
4-[4-(2-Dimethylamino-ethoxy)-phenylthio]-2-amino-aniline
4-[4-(3-Dimethylamino-propoxy)-phenylthio]-2-amino-aniline
4-[4-(4-Dimethylamino-butoxy)-phenylthio]-2-amino-aniline
4-[4-(2-Dimethylamino-1-methyl-ethoxy)-phenylthio]-2-amino-aniline
4-[4-(2-Dimethylamino-2-methyl-ethoxy)-phenylthio]-2-amino-aniline
4-[4-(2-Dimethylamino-1,2-dimethyl-ethoxy)-phenylthio]-2-amino-aniline
4-[4-(2-Dipropylamino-ethoxy)-phenylthio]-2-amino-aniline
4-[4-(3-Dipropylamino-propoxy)-phenylthio]-2-amino-aniline
4-[4-(4-Dipropylamino-butoxy)-phenylthio]-2-amino-aniline
4-[4-(2-Dipropylamino-1-methyl-ethoxy)-phenylthio]-2-amino-aniline
4-[4-(2-Dipropylamino-2-methyl-ethoxy)-phenylthio]-2-amino-aniline
4-[4-(2-Dipropylamino-1,2-dimethyl-ethoxy)-phenylthio]-2-amino-aniline
4-[4-(2-Diisopropylamino-ethoxy)-phenylthio]-2-amino-aniline
4-[4-(3-Diisopropylamino-propoxy)-phenylthio]-2-amino-aniline
4-[4-(4-Diisopropylamino-butoxy)-phenylthio]-2-amino-aniline
4-[4-(2-Diisopropylamino-1-methyl-ethoxy)-phenylthio]-2-amino-aniline
4-[4-(2-Diisopropylamino-2-methyl-ethoxy)-phenylthio]-2-amino-aniline
4-[4-(2-Diisopropylamino-1,2-dimethyl-ethoxy)-phenylthio]-2-amino-aniline
4-[4-(2-Dibutylamino-ethoxy)-phenylthio]-2-amino-aniline
4-[4-(3-Dibutylamino-propoxy)-phenylthio]-2-amino-aniline
4-[4-(4-Dibutylamino-butoxy)-phenylthio]-2-amino-aniline
4-[4-(2-Dibutylamino-1-methyl-ethoxy)-phenylthio]-2-amino-aniline
4-[4-(2-Dibutylamino-2-methyl-ethoxy)-phenylthio]-2-amino-aniline
4-[4-(2-Dibutylamino-1,2-dimethyl-ethoxy)-phenylthio]-2-amino-aniline
4-[4-(2-Pyrrolidyl-ethoxy)-phenylthio]-2-amino-aniline
4-[4-(3-Pyrrolidyl-propoxy)-phenylthio]-2-amino-aniline
4-[4-(4-Pyrrolidyl-butoxy)-phenylthio]-2-amino-aniline
4-[4-(2-Pyrrolidyl-1-methyl-ethoxy)-phenylthio]-2-amino-aniline
4-[4-(2-Pyrrolidyl-2-methyl-ethoxy)-phenylthio]-2-amino-aniline
4-[4-(2-Pyrrolidyl-1,2-dimethyl-ethoxy)-Phenylthio]-2-amino-aniline
4-[4-(2-Piperidyl-ethoxy)-phenylthio]-2-amino-aniline
4-[4-(3-Piperidyl-propoxy)-phenylthio]-2-amino-aniline
4-[4-(4-Piperidyl-butoxy)-phenylthio]-2-amino-aniline
4-[4-(2-Piperidyl-1-methyl-ethoxy)-phenylthio]-2-amino-aniline
4-[4-(2-Piperidyl-2-methyl-ethoxy)-phenylthio]-2-amino-aniline
4-[4-(2-Piperidyl-1,2-dimethyl-ethoxy)-phenylthio]-2-amino-aniline
4-[4-(2-Morpholyl-ethoxy)-phenylthio]-2-amino-aniline
4-[4-(3-Morpholyl-propoxy)-phenylthio]-2-amino-aniline
4-[4-(4-Morpholyl-butoxy)-phenylthio]-2-amino-aniline
4-[4-(2-Morpholyl-1-methyl-ethoxy)-phenylthio]-2-amino-aniline
4-[4-(2Morpholyl-2-methyl-ethoxy)-phenylthio]-2-amino-aniline
4-[4-(2-Morpholyl-1,2-dimethyl-ethoxy)-phenylthio]-2-amino-aniline
4-[3-(2-Dimethylamino-ethoxy)-phenylthio]-2-amino-aniline
4-[3-(3-Dimethylamino-propoxy)-phenylthio]-2-amino-aniline
4-[3-(4-Dimethylamino-butoxy)-phenylthio]-2-amino-aniline
4-[3-(2-Dimethylamino-1-methyl-ethoxy)-phenylthio]-2-amino-aniline
4-[3-(2-Dimethylamino-2-methyl-ethoxy)-phenylthio]-2-amino-aniline
4-[3-(2-Dimethylamino-1,2-dimethyl-ethoxy)-phenylthio]-2-amino-aniline
4-[3-(2-Dimethylamino-ethoxy)-phenylthio]-2-amino-aniline
4-[3-(3-Dimethylamino-propoxy)-phenylthio]-2-amino-aniline
4-[3-(4-Dimethylamino-butoxy)-phenylthio]-2-amino-aniline
4-[3-(2-Dimethylamino-1-methyl-ethoxy)-phenylthio]-2-amino-aniline
4-[3-(2-Dimethylamino-2-methyl-ethoxy)-phenylthio]-2-amino-aniline
4-[3-(2-Dimethylamino-1,2-dimethyl-ethoxy)-phenylthio]-2-amino-aniline 4-[3-(2-Dipropylamino-ethoxy)-phenylthio]-2-amino-aniline
4-[3-(3-Dipropylamino-propoxy)-phenylthio]-2-amino-aniline
4-[3-(4-Dipropylamino-butoxy)-phenylthio]-2-amino-aniline
4-[3-(2-Dipropylamino-1-methyl-ethoxy)-phenylthio]-2-amino-aniline
4-[3-(2-Dipropylamino-2-methyl-ethoxy)-phenylthio]-2-amino-aniline
4-[3-(2-Dipropylamino-1,2-dimethyl-ethoxy)-phenylthio]-2-amino-aniline
4-[3-(2-Diisopropylamino-ethoxy)-phenylthio]-2-amino-aniline
4-[3-(3-Diisopropylamino-propoxy)-phenylthio]-2-amino-aniline
4-[3-(4-Diisopropylamino-butoxy)-phenylthio]-2-amino-aniline
4-[3-(2-Diisopropylamino-1-methyl-ethoxy)-phenylthio]-2-amino-aniline
4-[3-(2-Diisopropylamino-2-methyl-ethoxy)-phenylthio]-2-amino-aniline
4-[3-(2-Diisopropylamino-1,2-dimethyl-ethoxy)-phenylthio]-2-amino-aniline
4-[3-(2-Dibutylamino-ethoxy)-phenylthio]-2-amino-aniline
4-[3-(3-Dibutylamino-propoxy)-phenylthio]-2-amino-aniline
4-[3-(4-Dibutylamino-butoxy)-phenylthio]-2-amino-aniline
4-[3-(2-Dibutylamino-1-methyl-ethoxy)-phenylthio]-2-amino-aniline
4-[3-(2-Dibutylamino-2-methyl-ethoxy)-phenylthio]-2-amino-aniline
4-[3-(2-Dibutylamino-1,2-dimethyl-ethoxy)-phenylthio]-2-amino-aniline
4-[3-(2-Pyrrolidyl-ethoxy)-phenylthio]-2-amino-aniline
4-[3-(3-Pyrrolidyl-propoxy)-phenylthio]-2-amino-aniline
4-[3-(4-Pyrrolidyl-butoxy)-phenylthio]-2-amino-aniline
4-[3-(2-Pyrrolidyl-1-methyl-ethoxy)-phenylthio]-2-amino-aniline
4-[3-(2-Pyrrolidyl-2-methyl-ethoxy)-phenylthio]-2-amino-aniline
4-[3-(2-Pyrrolidyl-1,2-dimethyl-ethoxy)-phenylthio]-2-amino-aniline
4-[3-(2-Piperidyl-ethoxy)-phenylthio]-2-amino-aniline
4-[3-(3-Piperidyl-propoxy)-phenylthio]-2-amino-aniline
4-[3-(4-Piperidyl-butoxy)-phenylthio]-2-amino-aniline
4-[3-(2-Piperidyl-1-methyl-ethoxy)-phenylthio]-2-amino-aniline
4-[3-(2-Piperidyl-2-methyl-ethoxy)-phenylthio]-2-amino-aniline
4-[3-(2-Piperidyl-1,2-dimethyl-ethoxy)-phenylthio]-2-amino-aniline
4-[3-(2-Morpholyl-ethoxy)-phenylthio]-2-amino-aniline
4-[3-(3-Morpholyl-propoxy)-phenylthio]-2-amino-aniline
4-[3-(4-Morpholyl-butoxy)-phenylthio]-2-amino-aniline
4-[3-(2-Morpholyl-1-methyl-ethoxy)-phenylthio]-2-amino-aniline
4-[3-(2-Morpholyl-2-methyl-ethoxy)-phenylthio]-2-amino-aniline
4-[3-(2-Morpholyl-1,2-dimethyl-ethoxy)-phenylthio]-2-amino-aniline
4-[2-(2-Dimethylamino-ethoxy)-phenylthio]-2-amino-aniline
4-[2-(3-Dimethylamino-propoxy)-phenylthio]-2-amino-aniline
4-[2-(4-Dimethylamino-butoxy)-phenylthio]-2-amino-aniline
4-[2-(2-Dimethylamino-1-methyl-ethoxy)-phenylthio]-2-amino-aniline
4-[2-(2-Dimethylamino-2-methyl-ethoxy)-phenylthio]-2-amino-aniline
4-[2-(2-Dimethylamino-1,2-dimethyl-ethoxy)-phenylthio]-2-amino-aniline
4-[2-(2-Di ethylamino-ethoxy)-phenylthio]-2-amino-aniline
4-[2-(3-Di ethylamino-propoxy)-phenylthio]-2-amino-aniline
4-[2-(4-Di ethylamino-butoxy)-phenylthio]-2-amino-aniline
4-[2-(2-Di-ethylamino-1-methyl-ethoxy)-phenylthio]-2-amino-aniline
4-[2-(2-Di-ethylamino-2-methyl-ethoxy)-phenylthio]-2-amino-aniline
4-[2-(2-Di-ethylamino-1,2-dimethyl-ethoxy)-phenylthio]-2-amino-aniline
4-[2-(2-Dipropylamino-ethoxy)-phenylthio]-2-amino-aniline
4-[2-(3-Dipropylamino-propoxy)-phenylthio]-2-amino-aniline
4-[2-(4-Dipropylamino-butoxy)-phenylthio]-2-amino-aniline
4-[2-(2-Dipropylamino-1-methyl-ethoxy)-phenylthio]-2-amino-aniline
4-[2-(2-Dipropylamino-2-methyl-ethoxy)-phenylthio]-2-amino-aniline
4-[2-(2-Dipropylamino-1,2-dimethyl-ethoxy)-phenylthio]-2-amino-aniline
4-[2-(2-Diisopropylamino-ethoxy)-phenylthio]-2-amino-aniline
4-[2-(3-Diisopropylamino-propoxy)-phenylthio]-2-amino-aniline
4-[2-(4-Diisopropylamino-butoxy)-phenylthio]-2-amino-aniline
4-[2-(2-Diisopropylamino-1-methyl-ethoxy)-phenylthio]-2-amino-aniline
4-[2-(2-Diisopropylamino-2-methyl-ethoxy)-phenylthio]-2-amino-aniline
4-[2-(2-Diisopropylamino-1,2-dimethyl-ethoxy)-phenylthio]-2-amino-aniline
4-[-2-(2-Dibutylamino-ethoxy)-phenylthio]-2-amino-aniline
4-[2-(3-Dibutylamino-propoxy)-phenylthio]-2-amino-aniline
4-[2-(4-Dibutylamino-butoxy)-phenylthio]-2-amino-aniline
4-[2-(2-Dibutylamino-1-methyl-ethoxy)-phenylthio]-2-amino-aniline
4-[2-(2-Dibutylamino-2-methyl-ethoxy)-phenylthio]-2-amino-aniline
4-[2-(2-Dibutylamino-1,2-dimethyl-ethoxy)-phenylthio]-2-amino-aniline
4-[2-(2-Pyrrolidyl-ethoxy)-phenylthio]-2-amino-aniline
4-[2-(3-Pyrrolidyl-propoxy)-phenylthio]-2-amino-aniline
4-[2-(4-Pyrrolidyl-butoxy)-phenylthio]-2-amino-aniline 4-[2-(2-Pyrrolidyl-1-methyl-ethoxy)-phenylthio]-2-amino-aniline
4-[2-(2-Pyrrolidyl-2-methyl-ethoxy)-phenylthio]-2-amino-aniline
4-[2-(2-Pyrrolidyl-1,2-dimethyl-ethoxy)-phenylthio]-2-amino-aniline
4-[2-(2-Piperidyl-ethoxy)-phenylthio]-2-amino-aniline
4-[2-(3-Piperidyl-propoxy)-phenylthio]-2-amino-aniline
4-[2-(4-Piperidyl-butoxy)-phenylthio]-2-amino-aniline
4-[2-(2-Piperidyl-1-methyl-ethoxy)-phenylthio]-2-amino-aniline
4-[2-(2-Piperidyl-2-methyl-ethoxy)-phenylthio]-2-amino-aniline
4-[2-(2-Piperidyl-1,2-dimethyl-ethoxy)-phenylthio]-2-amino-aniline
4-[2-(2-Morpholyl-ethoxy)-phenylthio]-2-amino-aniline
4-[2-(3-Morpholyl-propoxy)-phenylthio]-2-amino-aniline
4-[2-(4-Morpholyl-butoxy)-phenylthio]-2-amino-aniline
4-[2-(2-Morpholyl-1-methyl-ethoxy)-phenylthio]-2-amino-aniline
4-[2-(2-Morpholyl-2-methyl-ethoxy)-phenylthio]-2-amino-aniline
4-[2-(2-Morpholyl-1,2-dimethyl-ethoxy)-phenylthio-2-amino-aniline
4-[4-(2-Dimethylamino-ethoxy)-benzoyl]-2-amino-aniline
4-[4-(3-Dimethylamino-propoxy)-benzoyl]-2-amino-aniline
4-[4-(4-Dimethylamino-butoxy)-benzoyl]-2-amino-aniline
4-[4-(2-Dimethylamino-1-methyl-ethoxy)-benzoyl]-2-amino-aniline
4-[4-(2-Dimethylamino-2-methyl-ethoxy)-benzoyl]-2-amino-aniline
4-[4-(2-Dimethylamino-1,2-dimethyl-ethoxy)-benzoyl]-2-amino-aniline
4-[4-(2-Di-ethylamino-ethoxy)-benzoyl]-2-amino-aniline
4-[4-(3-Di-ethylamino-propoxy)-benzoyl]-2-amino-aniline
4-[4-(4-Di-ethylamino-butoxy)-benzoyl]-2-amino-aniline
4-[4-(2-Di-ethylamino-1-methyl-ethoxy)-benzoyl]-2-amino-aniline
4-[4-(2-Di-ethylamino-2-methyl-ethoxy)-benzoyl]-2-amino-aniline
4-[4-(2-Di-ethylamino-1,2-dimethyl-ethoxy)-benzoyl]-2-amino-aniline
4-[4-(2-Dipropylamino-ethoxy)-benzoyl]-2-amino-aniline
4-[4-(3-Dipropylamino-propoxy)-benzoyl]-2-amino-aniline
4-[4-(4-Dipropylamino-butoxy)-benzoyl]-2-amino-aniline
4-[4-(2-Dipropylamino-1-methyl-ethoxy)-benzoyl]-2-amino-aniline
4-[4-(2-Dipropylamino-2-methyl-ethoxy)-benzoyl]-2-amino-aniline
4-[4-(2-Dipropylamino-1,2-dimethyl-ethoxy)-benzoyl]-2-amino-aniline
4-[4-(2-Diisopropylamino-ethoxy)-benzoyl]-2-amino-aniline
4-[4-(3-Diisopropylamino-propoxy)-benzoyl]-2-amino-aniline
4-[4-(4-Diisopropylamino-butoxy)-benzoyl]-2-amino-aniline
4-[4-(2-Diisopropylamino-1-methyl-ethoxy)-benzoyl]-2-amino-aniline
4-[4-(2-Diisopropylamino-2-methyl-ethoxy)-benzoyl]-2-amino-aniline
4-[4-(2-Diisopropylamino-1,2-dimethyl-ethoxy)-benzoyl]-2-amino-aniline
4-[4-(2-Dibutylamino-ethoxy)-benzoyl]-2-amino-aniline
4-[4-(3-Dibutylamino-propoxy)-benzoyl]-2-amino-aniline
4-[4-(4-Dibutylamino-butoxy)-benzoyl]-2-amino-aniline
4-[4-(2-Dibutylamino-1-methyl-ethoxy)-benzoyl]-2-amino-aniline
4-[4-(2-Dibutylamino-2-methyl-ethoxy)-benzoyl]-2-amino-aniline
4-[4-(2-Dibutylamino-1,2-dimethyl-ethoxy)-benzoyl]-2-amino-aniline
4-[4-(2-Pyrrolidyl-ethoxy)-benzoyl]-2-amino-aniline
4-[4-(3-Pyrrolidyl-propoxy)-benzoyl]-2-amino-aniline
4-[4-(4-Pyrrolidyl-butoxy)-benzoyl]-2-amino-aniline
4-[4-(2-Pyrrolidyl-1-methylethoxy)-benzoyl]-2-amino-aniline
4-[4-(2-Pyrrolidyl-2-methyl-ethoxy)-benzoyl]-2-amino-aniline
4-[4-(2-Pyrrolidyl-1,2-dimethyl-ethoxy)-benzoyl]-2-amino-aniline
4-[4-(2-Piperidyl-ethoxy)-benzoyl]-2-amino-aniline
4-[4-(3-Piperidyl-propoxy)-benzoyl]-2-amino-aniline
4-[4-(4-Piperidyl-butoxy)-benzoyl]-2-amino-aniline
4-[4-(2-Piperidyl-1-methyl-ethoxy)-benzoyl]-2-amino-aniline
4-[4-(2-Piperidyl-2-methyl-ethoxy)-benzoyl]-2-amino-aniline
4-[4-(2-Piperidyl-1,2-dimethyl-ethoxy)-benzoyl]-2-amino-aniline
4-[4-(2-Morpholyl-ethoxy)-benzoyl]-2-amino-aniline
4-[4-(3-Morpholyl-propoxy)-benzoyl]-2-amino-aniline
4-[4-(4-Morpholyl-butoxy)-benzoyl]-2-amino-aniline
4-[4-(2-Morpholyl-1-methyl-ethoxy)-benzoyl-2-amino-aniline
4-[4-(2-Morpholyl-2-methyl-ethoxy)-benzoyl-2-amino-aniline
4-[4-(2-Morpholyl-1,2-dimethyl-ethoxy)-benzoyl]-2-amino-aniline
4-[3-(2-Dimethylamino-ethoxy)-benzoyl]-2-amino-aniline
4-[3-(3-Dimethylamino-propoxy)-benzoyl]-2-amino-aniline
4-[3-(4-Dimethylamino-butoxy)-benzoyl]-2-amino-aniline
4-[3-(2-Dimethylamino-1-methyl-ethoxy)-benzoyl]-2-amino-aniline
4-[3-(2-Dimethylamino-2-methyl-ethoxy)-benzoyl]-2-amino-aniline
4-[3-(2-Dimethylamino-1,2-dimethyl-ethoxy)-benzoyl]-2-amino-aniline
4-[3-(2-Di-ethylamino-ethoxy)-benzoyl]-2-amino-aniline
4-[3-(3-Di-ethylamino-propoxy)-benzoyl]-2-amino-aniline
4-[3-(4-Di-ethylamino-butoxy)-benzoyl]-2-amino-aniline
4-[3-(2-Di-ethylamino-1-methyl-ethoxy)-benzoyl]-2-amino-aniline 4-[3-(2-Di-ethylamino-2-methyl-ethoxy)-benzoyl]-2-amino-aniline
4-[3-(2-Di-ethylamino-1,2-dimethyl-ethoxy)-benzoyl]-2-amino-aniline
4-[3-(2-Dipropylamino-ethoxy)-benzoyl]-2-amino-aniline
4-[3-(3-Dipropylamino-propoxy)-benzoyl]-2-amino-aniline
4-[3-(4-Dipropylamino-butoxy)-benzoyl]-2-amino-aniline
4-[3-(2-Dipropylamino-1-methyl-ethoxy)-benzoyl]-2-amino-aniline
4-[3-(2-Dipropylamino-2-methyl-ethoxy)-benzoyl]-2-amino-aniline
4-[3-(2-Dipropylamino-1,2-dimethyl-ethoxy)-benzoyl]-2-amino-aniline
4-[3-(2-Diisopropylamino-ethoxy)-benzoyl]-2-amino-aniline
4-[3-(3-Diisopropylamino-propoxy)-benzoyl]-2-amino-aniline
4-[3-(4-Diisopropylamino-butoxy)-benzoyl]-2-amino-aniline
4-[3-(2-Diisopropylamino-1-methyl-ethoxy)-benzoyl]-2-amino-aniline
4-[3-(2-Diisopropylamino-2-methyl-ethoxy)-benzoyl]-2-amino-aniline
4-[3-(2-Diisopropylamino-1,2-dimethyl-ethoxy)-benzoyl]-2-amino-aniline
4-[3-(2-Dibutylamino-ethoxy)-benzoyl]-2-amino-aniline
4-[3-(3-Dibutylamino-propoxy)-benzoyl]-2-amino-aniline
4-[3-(4-Dibutylamino-butoxy)-benzoyl]-2-amino-aniline
4-[3-(2-Dibutylaminp-1-methyl-ethoxy)-benzoyl]-2-amino-aniline
4-[3-(2-Dibutylamino-2-methyl-ethoxy)-benzoyl]-2-amino-aniline
4-[3-(2-Dibutylamino-1,2-dimethyl-ethoxy)-benzoyl]-2-amino-aniline
4-[3-(2-Pyrrolidyl-ethoxy)-benzoyl]-2-amino-aniline
4-[3-(3-Pyrrolidyl-propoxy)-benzoyl]-2-amino-aniline
4-[3-(4-Pyrrolidyl-butoxy)-benzoyl]-2-amino-aniline
4-[3-(2-Pyrrolidyl-1-methyl-ethoxy)-benzoyl]-2-amino-aniline
4-[3-(2-Pyrrolidyl-2-methyl-ethoxy)-benzoyl]-2-amino-aniline
4-[3-(2-Pyrrolidyl-1,2-dimethyl-ethoxy)-benzoyl]-2-amino-aniline
4-[3-(2-Piperidyl-ethoxy)benzoyl]-2-amino-aniline
4-[3-(3-Piperidyl-propoxy)-benzoyl]-2-amino-aniline
4-[3-(4-Piperidyl-butoxy)-benzoyl]-2-amino-aniline
4-[3-(2-Piperidyl-1-methyl-ethoxy)-benzoyl]-2-amino-aniline
4-[3-(2-Piperidyl-2-methyl-ethoxy)-benzoyl]-2-amino-aniline
4-[3-(2-Piperidyl-1,2-dimethyl-ethoxy)-benzoyl]-2-amino-aniline
4-[3-(2-Morpholyl-ethoxy)-benzoyl]-2-amino-aniline
4-[3-(3-Morpholyl-propoxy)-benzoyl]-2-amino-aniline
4-[3-(4-Morpholyl-butoxy)-benzoyl]-2-amino-aniline
4-[3-(2-Morpholyl-1-methyl-ethoxy)-benzoyl]-2-amino-aniline
4-[3-(2-Morpholyl-2-methyl-ethoxy)-benzoyl]-2-amino-aniline
4-[3-(2-Morpholyl-1,2-dimethyl-ethoxy)-benzoyl]-2-amino-aniline
4-[2-(2-Dimethylamino-ethoxy)-benzoyl]-2-amino-aniline
4-[2-(3-Dimethylamino-propoxy)-benzoyl]-2-amino-aniline
4-[2-(4-Dimethylamino-butoxy)-benzoyl]-2-amino-aniline
4-[2-(2-Dimethylamino-1-methyl-ethoxy)-benzoyl]-2-amino-aniline
4-[2-(2-Dimethylamino-2-methyl-ethoxy)-benzoyl]-2-amino-aniline
4-[2-(Dimethylamino-1,2-dimethyl-ethoxy)-benzoyl]-2-amino-aniline 4-[2-(2-Di-ethylamino-ethoxy)-benzoyl]-2-amino-aniline
4-[2-(3-Di-ethylamino-propoxy)-benzoyl]-2-amino-aniline
4-[2-(4-Di-ethylamino-butoxy)-benzoyl]-2-amino-aniline
4-[2-(2-Di-ethylamino-1-methyl-ethoxy)-benzoyl]-2-amino-aniline
4-[2-Di-ethylamino-2-methyl-ethoxy)-benzoyl]-2-amino-aniline
4-[2-(2-Di-ethylamino-1,2-dimethyl-ethoxy)-benzoyl]-2-amino-aniline
4-[2-(2-Dipropylamino-ethoxy)-benzoyl]-2-amino-aniline
4-[2-(3-Dipropylamino-propoxy)-benzoyl]-2-amino-aniline
4-[2-(4-Dipropylamino-butoxy)-benzoyl]-2-amino-aniline
4-[2-(2-Dipropylamino-1-methyl-ethoxy)-benzoyl]-2-amino-aniline
4-[2-(2-Dipropylamino-2-methyl-ethoxy)-benzoyl]-2-amino-aniline
4-[2-(2-Dipropylamino-1,2-dimethyl-ethoxy)-benzoyl]-2-amino-aniline
4-[2-(2-Diisopropylamino-ethoxy)-benzoyl]-2-amino-aniline
4-[2-(3-Diisopropylamino-propoxy)-benzoyl]-2-amino-aniline
4-[2-(4-Diisopropylamino-butoxy)-benzoyl]-2-amino-aniline
4-[2-(2-Diisopropylamino-1-methyl-ethoxy)-benzoyl]-2-amino-aniline
4-[2-(2-Diisopropylamino-2-methyl-ethoxy)-benzoyl]-2-amino-aniline
4-[2-(2-Diisopropylamino-1,2-dimethyl-ethoxy)-benzoyl]-2-amino-aniline
4-[2-(2-Diisopropylamino-1,2-dimethyl-ethoxy)-benzoyl]-2-amino-aniline
4-[2-(2-Dibutylamino- thoxy)-benzoyl]-2-amino-aniline
4-[2-(3-Dibutylamino-propoxy)-benzoyl]-2-amino-aniline
4-[2-(4-Dibutylamino-butoxy)-benzoyl]-2-amino-aniline
4-[2-(2-Dibutylamino-1-methyl-ethoxy)-benzoyl]-2-amino-aniline
4-[2-(2-Dibutylamino-2-methyl-ethoxy)-benzoyl]-2-amino-aniline
4-[2-(2-Dibutylamino-1,2-dimethyl-ethoxy)-benzoyl]-2-amino-aniline
4-[2-(2-Pyrrolidyl-ethoxy)-benzoyl]-2-amino-aniline
4-[2-(3-Pyrrolidyl-propoxy)-benzoyl]-2-amino-aniline
4-[2-(2-(4-Pyrrolidyl-butoxy)-benzoyl]-2-amino-aniline
4-[2-(2-Pyrrolidyl-1-methylethoxy)-benzoyl]-2-amino-aniline 4-[2-(2-Pyrrolidyl-2-methyl-ethoxy)-benzoyl]-2-amino-aniline
4-[2-(2-Pyrrolidyl-1,2-dimethyl-ethoxy)-benzoyl]-2-amino-aniline
4-[2-(2-Piperidyl-ethoxy)-benzoyl]-2-amino-aniline
4-[2-(3-Piperidyl-propoxy)-benzoyl]-2-amino-aniline
4-[2-(4-Piperidyl-butoxy)-benzoyl]-2-amino-aniline
4-[2-(2-Piperidyl-1-methyl-ethoxy)-benzoyl]-2-amino-aniline
4-[2-(2-Piperidyl-2-methyl-ethoxy)-benzoyl]-2-amino-aniline
4-[2-(2-Piperidyl-1,2-dimethyl-ethoxy)-benzoyl]-2-amino-aniline
4-[2-(2-Morpholyl-ethoxy)-benzoyl]-2-amino-aniline
4-[2-(3-Morpholyl-propoxy)-benzoyl]-2-amino-aniline
4-[2-(4-Morpholyl-butoxy)-benzoyl]-2-amino-aniline
4-[2-(2-Morpholyl-1-methyl-ethoxy)-benzoyl]-2-amino-aniline
4-[2-(2-Morpholyl-2-methyl-ethoxy)-benzoyl]-2-amino-aniline
4-[2-(2-Morpholyl-1,2-dimethyl-ethoxy)-benzoyl]-2-amino-aniline To react the reactants a temperature of from 30° to 100° C is advantageous. The reaction time may be between 30 minutes and 10 hours. As a by-product the methyl-mercaptan is set free. The basically substituted 2-carbalkoxy-amino-benzimidazolyl-5-(6)-phenyl ethers and -ketones are isolated in usual way, expediently by diluting with water and mixing with ammonia until alkaline reaction.

With the o-phenylene-diamino derivatives of the formula (2) mentioned above the following products of the formula (1) are obtained by the reaction according to a):

4-(2-Dimethylamino-ethoxy)-phenyl-2-carbomethoxyamino-benzimidazolyl-5(6)-ether
4-(3-Dimethylamino-propoxy)-phenyl-2-carbomethoxyamino-benzimidazolyl-5(6)-ether
4-(4-Dimethylamino-butoxy)-phenyl-2-carbomethoxyamino-benzimidazolyl-5(6)-ether
4-(2-Dimethylamino-1-methyl-ethoxy)-phenyl-2-carbomethoxyamino-benzimidazolyl-5(6)-ether
4-(2-Dimethylamino-2-methyl-ethoxy)-phenyl-2-carbomethoxyamino-benzimidazolyl-5(6)-ether
4-(2-Dimethylamino-1,2-dimethyl-ethoxy)-phenyl-2-carbomethoxy-amino-benzimidazolyl-5(6)-ether
4-(2-Dimethylamino-ethoxy)-phenyl-2-carbomethoxyamino-benzimidazolyl-5(6)-ether
4-(3-Dimethylamino-propoxy)-phenyl-2-carbomethoxyamino-benzimidazolyl-5(6)-ether
4-(4-Dimethylamino-butoxy)-phenyl-2-carbomethoxyamino-benzimidazolyl-5(6)-ether
4-(2-Dimethylamino-1-methyl-ethoxy)-phenyl-2-carbomethoxyamino-benzimidazolyl-5(6)-ether
4-(2-Dimethylamino-2-methyl-ethoxy)-phenyl-2-carbomethoxyamino-benzimidazolyl-5(6)-ether
4-(2-Dimethylamino-1,2-dimethyl-ethoxy)-phenyl-2-carbomethoxy-amino-benzimidazolyl-5(6)-ether
4-(2-Dipropylamino-ethoxy)-phenyl-2-carbomethoxyamino-benzimidazolyl-5(6)-ether
4-(3-Dipropylamino-propoxy)-phenyl-2-carbomethoxyamino-benzimidazolyl-5(6)-ether
4-(4-Dipropylamino-butoxy)-phenyl-2-carbomethoxyamino-benzimidazolyl-5(6)-ether
4-(2-Dipropylamino-1-methyl-ethoxy)-phenyl-2-carbomethoxyamino-benzimidazolyl-5(6)-ether
4-(2-Dipropylamino-2-methyl-ethoxy)-phenyl-2-carbomethoxyamino-benzimidazolyl-5(6)-ether
4-(2-Dipropylamino-1,2-dimethyl-ethoxy)-phenyl-2-carbomethoxy-amino-benzimidazolyl-5(6)-ether
4-(2-Diisopropylamino-ethoxy)-phenyl-2-carbomethoxyamino-benzimidazolyl-5(6)-ether
4-(3-Diisopropylamino-propoxy)-phenyl-2-carbomethoxyamino-benzimidazolyl-5(6)-ether
4-(4-Diisopropylamino-butoxy)-phenyl-2-carbomethoxyamino-benzimidazolyl-5(6)-ether
4-(2-Diisopropylamino-1-methyl-ethoxy)-phenyl-2-carbomethoxy-amino-benzimidazolyl-5(6)-ether
4-(2-Diisopropylamino-2-methyl-ethoxy)-phenyl-2-carbomethoxy-amino-benzimidazolyl-5(6)-ether
4-(2-Diisopropylamino-1,2-dimethyl-ethoxy)-phenyl-2-carbomethoxy-amino-benzimidazolyl-5(6)-ether
4-(2-Dibutylamino-ethoxy)-phenyl-2-carbomethoxyamino-benzimidazolyl-5(6)-ether
4-(3-Dibutylamino-propoxy)-phenyl-2-carbomethoxyamino-benzimidazolyl-5(6)-ether
4-(4-Dibutylamino-butoxy)-phenyl-2-carbomethoxyamino-benzimidazolyl-5(6)-ether
4-(2-Dibutylamino-1-methyl-ethoxy)-phenyl-2-carbomethoxy-amino-benzimidazolyl-5(6)-ether
4-(2-Dibutylamino-2-methyl-ethoxy)-phenyl-2-carbomethoxy-amino-benzimidazole-5(6)-ether
4-(2-Dibutylamino-1,2-dimethyl-ethoxy)-phenyl-2-carbomethoxy-amino-benzimidazolyl-5(6)-ether
4-(2-Pyrrolidyl-ethoxy)-phenyl-2-carbomethoxyamino-benzimidazolyl-5(6)-ether
4-(3-Pyrrolidyl-propoxy)-phenyl-2-carbomethoxyamino-benzimidazolyl-5(6)-ether
4-(4-Pyrrolidyl-butoxy)-phenyl-2-carbomethoxyamino-benzimidazolyl-5(6)-ether
4-2-Pyrrolidyl-1-methyl-ethoxy)-phenyl-2-carbomethoxyamino-benzimidazolyl-5(6)-ether
4-(2-Pyrrolidyl-2-methyl-ethoxy)-phenyl-2-carbomethoxyamino-benzimidazolyl-5(6)-ether
4-(2-Pyrrolidyl-1,2-dimethyl-ethoxy)-phenyl-2-carbomethoxyamino-benzimidazolyl-5(6)-ether
4-(2-Piperidyl-ethoxy)-phenyl-2-carbomethoxyamino-benzimidazolyl-5(6)-ether
4-(3-Piperidyl-propoxy)-phenyl-2-carbomethoxyamino-benzimidazolyl-5(6)-ether
4-(4-Piperidyl-butoxy)-phenyl-2-carbomethoxyamino-benzimidazolyl-5(6)-ether
4-(2-Piperidyl-1-methyl-ethoxy)-phenyl-2-carbomethoxyamino-benzimidazolyl-5(6)-ether
4-(2-Piperidyl-2-methyl-ethoxy)-phenyl-2-carbomethoxyamino-benzimidazolyl-5(6)-ether
4-(2-Piperidyl-1,2-dimethyl-ethoxy)-phenyl-2-carbomethoxyamino-benzimidazolyl-5(6)-ether
4-(2-Morpholyl-ethoxy)-phenyl-2-carbomethoxyamino-benzimidazolyl-5(6)-ether
4-(3-Morpholyl-propoxy)-phenyl-2-carbomethoxyamino-benzimidazolyl-5(6)-ether
4-(4-Morpholyl-butoxy)-phenyl-2-carbomethoxyamino-benzimidazolyl-5(6)-ether
4-(2-Morpholyl-1-methyl-ethoxy)-phenyl-2-carbomethoxyamino-benzimidazolyl-5(6)-ether
4-(2-Morpholyl-2-methyl-ethoxy)-phenyl-2-carbomethoxyamino-benzimidazolyl-5(6)-ether
4-(2-Morpholyl-1,2-dimethyl-ethoxy)-phenyl-2-carbomethoxyamino-benzimidazolyl-5(6)-ether
3-(2-Dimethylamino-ethoxy)-phenyl-2-carbomethoxyamino-benzimidazolyl-5(6)-ether
3-(3-Dimethylamino-propoxy)-phenyl-2-carbomethoxyamino-benzimidazolyl-5(6)-ether
3-(4-dimethylamino-butoxy)-phenyl-2-carbomethoxyamino-benzimidazolyl-5(6)-ether 3-(2-Dimethylamino-1-methyl-ethoxy)-phenyl-2-carbomethoxyamino-benzimidazolyl-5(6)-ether
3-(2-Dimethylamino-2-methyl-ethoxy)-phenyl-2-carbomethoxyamino-benzimidazolyl-5(6)-ether
3-(2-Dimethylamino-1,2-dimethyl-ethoxy)-phenyl-2-carbomethoxy-amino-benzimidazolyl-5(6)-ether
3-(2-Dimethylamino-ethoxy)-phenyl-2-carbomethoxyamino-benzimidazolyl-5(6)-ether
3-(3-Dimethylamino-propoxy)-phenyl-2-carbomethoxyamino-benzimidazolyl-5(6)-ether
3-(4-Dimethylamino-butoxy)-phenyl-2-carbomethoxyamino-benzimidazolyl-5(6)-ether
3-(2-Dimethylamino-1-methyl-ethoxy)-phenyl-2-carbomethoxyamino-benzimidazolyl-5(6)-ether
3-(2-Dimethylamino-2-methyl-ethoxy)-phenyl-2-carbomethoxyamino-benzimidazolyl-5(6)-ether
3-(2-Dimethylamino-1,2-dimethyl-ethoxy)-phenyl-2-carbomethoxy-amino-benzimidazolyl-5(6)-ether
3-(2-Dipropylamino-ethoxy)-phenyl-2-carbomethoxyamino-benzimidazolyl-5(6)-ether
3-(3-Dipropylamino-propoxy)-phenyl-2-carbomethoxyamino-benzimidazolyl-5(6)-ether
3-(4-Dipropylamino-butoxy)-phenyl-2-carbomethoxyamino-benzimidazolyl-5(6)-ether
3-(2-dipropylamino-1-methyl-ethoxy)-phenyl-2-carbomethoxyamino-benzimidazolyl-5(6)-ether
3-(2-dipropylamino-1,2-dimethyl-ethoxy)-phenyl-2-carbomethoxy-amino-benzimidazolyl-5(6)-ether
3-(2-Diisopropylamino-ethoxy)-phenyl-2-carbomethoxyamino-benzimidazolyl-5(6)-ether
3-(3-Diisopropylamino-propoxy)-phenyl-2-carbomethoxyamino-benzimidazolyl-5(6)-ether
3-(4-Diisopropylamino-butoxy)-phenyl-2-carbomethoxyamino-benzimidazolyl-5(6)-ether
3-(2-Diisopropylamino-1-methyl-ethoxy)-phenyl-2-carbomethoxy-amino-benzimidazolyl-5(6)-ether
3-(2-Diisopropylamino-2-methyl-ethoxy)-phenyl-2-carbomethoxy-amino-benzimidazolyl-5(6)-ether
3-(2-Diisopropylamino-1,2-dimethyl-ethoxy)-phenyl-2-carbomethoxy-amino-benzimidazolyl-5(6)ether
3-(2-Dibutylamino-ethoxy)-phenyl-2-carbomethoxyamino-benzimidazolyl-5(6)-ether
3-(3-Dibutylamino-propoxy)-phenyl-2-carbomethoxyamino-benzimidazolyl-5(6)-ether
3-(4-Dibutylamino-butoxy)-phenyl-2-carbomethoxyamino-benzimidazolyl-5(6)-ether
3-(2-Dibutylamino-1-methyl-ethoxy)-phenyl-2-carbomethoxyamino-benzimidazolyl-5(6)-ether
3-(2-Dibutylamino-2-methyl-ethoxy)-phenyl-2-carbomethoxyamino-benzimidazolyl-5(6)-ether
3-(2-Dibutylamino-1,2-dimethyl-ethoxy)-phenyl-2-carbomethoxy-amino-benzimidazolyl-5(6)-ether
3-(2-Pyrrolidyl-ethoxy)-phenyl-2-carbomethoxyamino-benzimidazolyl-5(6)-ether
3-(3-Pyrrolidyl-propoxy)-phenyl-2-carboemthoxyamino-benzimidazolyl-5(6-ether
4-Pyrrolidyl-butoxy)-phenyl-2-carbomethoxyamino-benzimidazolyl-5-(6)-ether
3-(2-Pyrrolidyl-1-methyl-ethoxy)-phenyl-2-carbomethoxyamino-benzimidazolyl-5(6)-ether
3-(2-Pyrrolidyl-2-methyl-ethoxy)-phenyl-2-carbomethoxyamino-benzimidazolyl-5(6)-ether
3-(2-Pyrrolidyl-1,2-dimethyl-ethoxy)-phenyl-2-carbomethoxyamino-benzimidazolyl-5(6)-ether
3-(2-Piperidyl-ethoxy)-phenyl-2-carbomethoxyamino-benzimidazolyl-5(6)-ether
3-(3-Piperidyl-propoxy)-phenyl-2-carbomethoxyamino-benzimidazolyl-5(6)-ether
3-(4-Piperidyl-butoxy)-phenyl-2-carbomethoxyamino-benzimidazolyl-5(6)-ether
3-(2-Piperidyl-1-methyl-ethoxy)-phenyl-2-carbomethoxyamino-benzimidazoyl-5(6)-ether
3-(2-Piperidyl-2-methyl-ethoxy)-phenyl-2-carbomethoxyamino-benzimidazolyl-5(6)-ether
3-(2-Piperidyl-1,2-dimethyl-ethoxy)-phenyl-2-carbomethxyamino-benzimidazolyl-5(6)-ether
3-(2-Morpholyl-ethoxy)-phenyl-2-carbomethoxyamino-benzimidazolyl-5(6)-ether
3-(3-Morpholyl-propoxy)-phenyl-2-carbomethoxyamino-benzimidazolyl-5(6)-ether
3-(4-Morpholyl-butoxy)-phenyl-2-carbomethoxyamino-benzimidazolyl-5(6)-ether
3-(2-Morpholyl-1-methyl-ethoxy)-phenyl-2-carbomethoxyamino-benzimidazolyl-5(6)-ether
3-(2-Morpholyl-2-methyl-ethoxy)-phenyl-2-carbomethoxyamino-benzimidazolyl-5(6)-ether
3-(2-Morpholyl-1,2-dimethyl-ethoxy)-phenyl-2-carbomethoxyamino-benzimidazolyl-5(6)-ether
2-(2-Dimethylamino-ethoxy)-phenyl-2-carbomethoxyamino-benzimidazolyl-5(6)-ether
2-(3-Dimethylamino-propoxy)-phenyl-2-carbomethoxyamino-benzimidazolyl-5(6)-ether
2-(4-Dimethylamino-butoxy)-phenyl-2-carbomethoxyamino-benzimidazolyl-5(6)-ether
2-(2-Dimethylamino-1-methyl-ethoxy)-phenyl-2-carbomethoxyamino-benzimidazolyl-5(6)-ether
2-(2-Dimethylamino-2-methyl-ethoxy)-phenyl-2-carbomethoxyamino-benzimidazolyl-5(6)-ether
2-(2-Dimethylamino-1-dimethyl-ethoxy)-phenyl-2-carbomethoxyamino-benzimidazolyl-5(6)-ether
2-(2-Dimethylamino-ethoxy)-phenyl-2-carbomethoxyamino-benzimidazolyl-5(6)-ether
2-(3-Dimethylamino-propoxy)-phenyl-2-carbomethoxyamino-benzimidazolyl-5(6)-ether
2-(4-Dimethylamino-butoxy)-phenyl-2-carbomethoxyamino-benzimidazolyl-5(6)-ether
2-(2-Dimethylamino-1-methyl-ethoxy)-phenyl-2-carbomethoxyamino-benzimidazolyl-5(6)-ether
2-(2-Dimethylamino-2-methyl-ethoxy)-phenyl-2-carbomethoxyamino-benzimidazolyl-5(6)-ether
2-(2-Dimethylamino-1,2-dimethyl-ethoxy)-phenyl-2-carbomethoxy-amino-benzimidazolyl-5(6)-ether
2-(2-Dipropylamino-ethoxy)-phenyl-2-carbomethoxyamino-benzimidazolyl-5(6)-ether
2-(3-Dipropylamino-propoxy)-phenyl-2-carbomethoxyamino-benzimidazolyl-5(6)-ether
2-(4-Dipropylamino-butoxy)-phenyl-2-carbomethoxyamino-benzimidazolyl-5(6)-ether
2-(2-Dipropylamino-1-methyl-ethoxy)-phenyl-2-carbomethoxyamino-benzimidazolyl-5(6)-ether
2-(2-Dipropylamino-2-methyl-ethoxy)-phenyl-2-carbomethoxyamino-benzimidazolyl-5(6)-ether
2-(2-Dipropylamino-1,2-dimethyl-ethoxy)-phenyl-2-carbomethoxy-amino-benzimidazolyl-5(6)-ether
2-(2-Diisopropylamino-ethoxy)-phenyl-2-carbomethoxyamino-benzimidazolyl-5(6)-ether
2-(3-Diisopropylamino-propoxy)-phenyl-2-carbomethoxyamino-benzimidazolyl-5(6)-ether
2-(4-Diisopropylamino-butoxy)-phenyl-2-carbomethoxyamino-benzimidazolyl-5(6)-ether
2-(2-Diisopropylamino-1-methyl-ethoxy)-phenyl-2-carbomethoxy-amino-benzimidazolyl-5(6)-ether
2-(2-Diisopropylamino-2-methyl-ethoxy)-phenyl-2-carbomethoxy-benzimidazolyl-5(6)-ether
2-(Diisopropylamino-1,2-dimethyl-ethoxy)-phenyl-2-carbomethoxy-benzimidazolyl-5(6)-ether 2-(2-Dibutylamino-ethoxy)-phenyl-2-carbomethox-
   yamino-benzimidazolyl-5(6)-ether
2-(3-Dibutylamino-propoxy)-phenyl-2-carbomethox-
   yamino-benzimidazolyl-5(6)-ether
2-(4-Dibutylamino-butoxy)-phenyl-2-carbomethox-
   yamino-benzimidazolyl-5(6)-ether
2-(2-Dibutylamino-1-methyl-ethoxy)-phenyl-2-car-
   bomethoxyamino-benzimidazolyl-5(6)-ether
2-(2-Dibutylamino-2-methyl-ethoxy)-phenyl-2-car-
   bomethoxyamino-benzimidazolyl-5(6)-ether
2-(2-Dibutylamino-1,2-dimethyl-ethoxy)-phenyl-2-
   carbomethoxyamino-benzimidazolyl-5(6)-ether
2-(2-Pyrrolidyl-ethoxy)-phenyl-2-carbomethox-
   yamino-benzimidazolyl-5(6)-ether
2-(3-Pyrrolidyl-propoxy)-phenyl-2-carbomethox-
   yamino-benzimidazolyl-5(6)-ether
2-(4-Pyrrolidyl-butoxy)-phenyl-2-carbomethox-
   yamino-benzimidazolyl-5(6)-ether
2-(2-Pyrrolidyl-1-methyl-ethoxy)-phenyl-2-carbome-
   thoxyamino-benzimidazolyl-5(6)-ether
2-2-Pyrrolidyl-2-methyl-ethoxy)-phenyl-2-carbome-
   thoxyamino-benzimidazolyl-5(6)-ether
2-(2-Piperidyl-ethoxy)-phenyl-2-carbomethoxyamino-
   benzimidazolyl-5(6)-ether
2-(3-Piperidyl-propoxy)-phenyl-2-carbomethox-
   yamino-benzimidazolyl-5(6)-ether
2-(4-Piperidyl-butoxy)-phenyl-2-carbomethoxyamino-
   benzimidazolyl-5(6)-ether
2-(2-Piperidyl-1-methyl-ethoxy)-phenyl-2-carbome-
   thoxyamino-benzimidazolyl-5(6)-ether
2-(2-Piperidyl-2-methyl-ethoxy)-phenyl-2-carbome-
   thoxyamino-benzimidazolyl-5(6)-ether
2-(2-Piperidyl-1,2-dimethyl-ethoxy)-phenyl-2-car-
   bomethoxy-amino-benzimidazolyl-5(6)-ether
2-(2-Morpholyl-ethoxy)-phenyl-2-carbomethox-
   yamino-benzimidazolyl-5(6)-ether
2-(3-Morpholyl-propoxy)-phenyl-2-carbomethox-
   yamino-benzimidazolyl-5(6)-ether
2-(4-Morpholyl-butoxy)-phenyl-2-carbomethox-
   yamino-benzimidazolyl-5(6)-ether
2-(2-Morpholyl-1-methyl-ethoxy)-phenyl-2-carbome-
   thoxyamino-benzimidazolyl-5(6)-ether
2-(2-Morpholyl-2-methyl-ethoxy)-phenyl-2-carbome-
   thoxyamino-benzimidazolyl-5(6)-ether
2-(2-Morpholyl-1,2-dimethyl-ethoxy)-phenyl-2-car-
   bomethoxyamino-benzimidazolyl-5(6)-ether Furthermore, by the reaction according to a) there are obtained the 2-carbethoxyamino-, 2-carbopropoxyamino-, 2-carboisopropoxyamino-, 2-carbobutoxyamino-, 2-carbo-secondary-butoxyamino- and 2-carbo-tertiary-butoxy-amino-anologous compounds corresponding to the above-mentioned compounds, as well as analogous thioethers and ketones from all compounds mentioned.

To carry out the reaction according to b) a chloroformic acid ester of the formula (9) as it is alos used for the process according to a) is added to an aqueous suspension of cyanamide in form of a salt, preferably of the calcium salt (10), whereby the reaction temperature is maintained between 40° and 60° C by cooling.

After filtering dark by-products which have precipitated, the cyanamide carboxylate of the formula (4), is obtained.

The cyanamide carboxylate (4) thus obtained is mixed with an o-phenylene-diamino-derivative (2) and by adjusting a mineral acid, for example concentrated hydrochloric acid, the mixture is adjusted to a pH-value of from 1 to 6, preferably of from 2 to 4. For reaction the mixture is expediently maintained between 30 and 100° C, and depending on the reactivity of the o-phenylene-diamino derivative between 30 minutes and 10 hours. After cooling the reaction mixture the reaction product precipitated (1) is isolated by filtrating and washing.

The o-phenylene-diamino derivative (2) may be reacted as a free amine in the manner indicated above with an alkyl-S-methyl-thio-urea-carboxylate (3) or in form of the acid addition salt thereof with a suitable organic or mineral acid such as hydrochloric acid, sulfuric acid, acetic acid, oxalic acid or similar acids.

To carry out the reaction according to c) 1 mol of the o-phenylene-diamino-derivative of the formula (2) is expediently reacted with one mole of the bis-alkyl- or bis-arylthio-methyleneamino-formic acid ester in an inert solvent such as tetrahydrofuran, dioxan, isopropyl ether or chloroform at elevated temperature, advantageously of the boiling temperature of the solvent used.

According to the process of the invention the bis-alkyl or arylthio-methylene-amino-formic acid ester may also be prepared only in the reaction vessel from the hydrochloride of the imino-dithio-carbonic acid ester by adding a chloroformic acid ester of the formula (9), as it is also used to carry out the process according to a).

In this case an acid acceptor must be present which may be an organic or inorganic base, such as sodium hydroxide, sodium bicarbonate or triethyl amine. As reaction medium there are suitable polar or non-polar solvents such as ether, acetone, dioxan, water, dimethylformamide, benzene or cyclohexane, whereby the temperature is preferably not allowed to exceed 20° C.

The bis-alkyl- or bis-arylthio-methyleneamino-formic acid esters may be prepared from the corresponding dithio-iminocarbonic acid esters by reaction with chloroformic acid esters of the formual (9) according to U.S. Pat. No. 3,562,290.

As examples of bis-alkyl- or bis-arylthio-methyleneaminoformic acid ester ther may be mentioned:
the bis-methylthio-methylenamino-formic acid-methyl ester,
the bis-methylthio-methylenamino-formic acid-ethyl ester,
the bis-methylthio-methylenamino-formic acid-propyl ester,
the bis-methylthio-methylenamino-formic acid-isopropyl ester,
the bis-methylthio-methylenamino-formic acid-butyl ester,
the bis-methylthio-methylenamino-formic acid-sec. butyl ester,
the bis-butylthio-methylenamino-formic acid-methyl ester,
the methylthio-butylthio-methylamino-formic acid-methyl ester,
the allythio-cyclohexythoi-methylenamino-formic acid-methyl ester,
the methylthio-phenylthio-methylenamino-formic acid-methyl ester,
the methylthio-(3,4-dichloro-benzyl-thio)-methylenamino-formic acid-methyl ester or
the methylthio-(2-chloro-4-methylphenythio)-methyleneamino-formic acid methyl ester.

The o-phenylene-diamino derivative of the formula (2) serving as starting material is obtained by reduction of a corresponding amino-nitro derivative of the formula (11), wherein X and Y have the same meaning as in formula (1). The reduction may be effected for example by hydrogenation in the presence of Raney-Nickel and of a solvent such as methanol or dimethylformamide at temperatures between 20 and 60° C or by treatment with reduced agents such as sodium dithionite.

The amino-nitro-derivatives of the formula (11) are heated by reaction of the corresponding hydroxynitramino-diphenyl ethers of the formula (13), wherein X has the same meaning as in formula (1), expediently in form of the alkali salt thereof, preferably of the sodium salt, with an alkaline compound of the formula (12), wherein Y has the same meaning as in formula (1) and W is a final group such as halogen, for example chlorine, bromine or iodine, or the radical of an organic or inorganic oxygen-containing acid, such as a sulfate or p-toluene-sulfonic acid group, in an expediently aprotic dipolar solvent such as acetone, dimethylformamide or dimethylsulfoxide or in an alcohol such as methanol or ethanol, up to a higher temperature, preferably the boiling point of the solvent used. When the reaction is finished, the solvent is removed by distillation and the residue is worked up after treating with a base, advantageously ammonia or an alkali hydroxide such as sodium hydroxide, while using a solvent not miscible with water, such as ethyl acetate, methylene dichloride or chloroform.

By treating the corresponding methoxy derivatives of the formula (14), wherein X has the same meaning as in formula (1), the hydroxy-nitramino-diphenly ethers of the formula (13) are treated with strong mineral acids, preferably hydrobromic acid or organic compounds capable of splitting off such acids, as for example pyridine hydrochloride, at an elevated temperature, preferably the boiling point of the aqueous solution of this acid or of the solution of the salt-like organic compound in the base which is the starting compound thereof, for example pyridine in the case of the pyridine hydrochloride and the reaction product is isolated by dilution with water.

The substances claimed according to the invention are valuable chemotherapeutic agents and are suitable for treating parasitic diseases in humans and animals. These compositions display a particular activity against ankylostomes, but they have also an excellent activity against other helminths, as for example Haemonchus, Ostertaiga, Hyostrongylus, Trichostrongylus, Cooperia (Fasciola hepatica) and many others. The compounds have a particularly pronounced activity aganist hook worms, which attack, above all, ruminants and cause considerable damage to health and considerable economic losses.

The compounds of the formula (1) may be used as anthelmintics in human and veterinary medicine. Depending on the case they are administered for one to 14 days between 0.5 and 50 mg per kg of body weight.

For oral application tablets, dragees, capsules, powders, granules or pastes are considered, which contain the active substances together with usual auxiliaries and carriers such as starch, cellulose power, talc, magnesium stearate, sugar, gelatin, calcium carbonate, finely divided silicic acid, carboxymethyl cellulose or similar substances.

For parenteral application there are considered solutions, for example oily solutions which are prepared while using sesame oil, castor oil or synthetic triglycerides, if desired with addition of tocopherol as anti-oxidizing agent and/or while using surface-active substances such as sorbitane-fatty acid ester. Aqueous suspension are considered, which are prepared while using ethoxylated sorbitane-fatty acid esters, if desired with addition or thickening agents, such as polyethylene glycol or carboxymethyl cellulose.

The concentrations of the active substances according to the invention in the composition prepared with these substances are preferably between 2 and 20 percent by weight for being used as veterinary medicament; for the use as human medicament the concentrations of the active substances preferably range between 20 and 80 percent by weight.

To determine the action of the compounds according to the invention, chemotherapeutic investigations on either sheep or dogs are carried out. The former are experimentally infected with larvae of Haemonchus contortus and Trichostrongylus colubriformis, and the latter with larvae of Ancylostoma canium. The test animals are kept in tiled boxes which are thoroughly cleaned daily to avoid super-infections. At the end of the pre-patency period (time between infection and sexual maturity of the parasites, with incipient elimination or reproduction products), the number of eggs per gram of faeces (EpG) are determined by a modified McMaster process (see Tierarztliche Umschau 6, 209 – 210; 1951). Immediately thereafter, the animals – in general comprising four to eight animals per group, but at least two – are treated orally or subcutaneously, a suspension of 0.5 to 10.0 mg/kg of body weight in 10 ml of a tylose suspension (1% strength aqueous suspension) being administered. On the 7th, 14th and 28th day after the treatment, the number of eggs per gram of faeces is again determined in accordance with the abovementioned process and its change in percentage terms relative to the initial value before treatment is determined. In cases of convincing success, dissection of the test animals nd examination of the digestive tract for any nematodes present is optionally carried out.

The tests had the following effects:

| Compound acc. to Example | Parasite | Dosage unit in mg/kg perorally | killed parasites in % |
|---|---|---|---|
| 1 | Fasciola hepatica | 30 | 100 |
| 1 | Hook worms | 10 | 100 |
| 2 | Fasciola hepatica | 30 | 100 |
| 2 | Hook worms | 10 | 100 |
| 4 | Hook worms | 10 | > 90 |
| 5 | Trichostrongylus | 2.5 | 100 |
| 7 | Hook worms | 20 | 100 |
| 9 | Hook worms | 20 | 100 |
| 13 | Hook worms | 20 | 100 |
| 16 | Hook worms | 20 | 100 |

The products of the invention act against hook worms and the group of the gastro-intestinal stronglyides down to dosage units of less than 10 mg/kg. They are superior to the known 5(6)-substituted 2-benzimidazol -carbaminates especially by the combined activity with a relatively small dosage unit for the treatment of multiple infections.

The following Examples illustrate the invention.

EXAMPLE 1

(Process a)

To a well-stirred mixture of 13.2 g of S-methyl-thiourea-sulfate in 20 ml of water and 8 ml of chloroformic acid methyl ester 27.5 g of a 25% sodium hydroxide solution were added, while cooling with ice, at a temperature of not more than 10° C. Stirring was continued for half an hour and then a mixture of 24 ml of glacial acetic acid and 120 ml of water was added.

15.5 g of 4-[3-(2-piperidyl-ethoxy]-2-amino-aniline, dissolved in 120 ml of isopropanol were added and the mixture was refluxed for two hours. The hot solution was mixed dropwise with concentrated ammonia until an alkaline reactions was obtained whereby a thick slurry precipitated.

The whole was suction-filtered and the crude product was purified by dissolving in a mixture of 250 ml of methanol and 20 ml of a 2N hydrochloric acid at 50° C, filtering with coal and precipitating again with ammonia. The pure 3-(2-piperidyl-ethoxy)-phenyl-2-carbomethoxyamino-benzimidazolyl-5(6)-ether was suction filtered and washed out with methanol and then with water.

Yield: 13.g. Melting point: 200° C with decomposition.

To prepare the 4-[3-(2-piperidyl-ethoxy)-phenoxy]-2-amino-aniline 17 g of 4-[3-(2-piperidy-ethoxy]-2-amino-nitrobenzene were hydrogenated in 200 ml of dimethylformamide in the presence of Raney-Nickel at 50° C and a hydrogen pressure of 50 atmospheres gauge. The catalyst was filtered and the filtrate was evaporated until dry. After diluting with isopropanol the crude 4-[3-(2-piperidyl-ethoxy)-phenoxy]-2-aminoaniline can be used directly in the above-described reaction with S-methyl-thio-urea sulfate.

To prepare the 4-[3-(2-piperidyl-ethoxy)-phenoxy]-2-amino-nitrobenzene 6 g of sodium were dissolved first in 500 ml of absolute ethanol, 64 g of 4-(3-hydroxy-phenoxy)-2-aminonitrobenzene were added and the solution was concentrated in vacuo. After drying over solid caustic potash 70 g of the sodium salt of the 4-(3-hydroxy-phenoxy)-2-amino-nitrobenzene were obtained.

A mixture of 13.4 g of the sodium salt of 4-(3-hydroxyphenoxy)-2-amino-nitrobenzene in 100 ml of acetone was stirred with 7.5 g of piperidino-ethyl-chloride for three hours on on steam bath. Then the solvent was evaporated under reduced pressure, the residue was dissolved in diluted acetic acid and the solution was made alkaline with ammonia. To isolate the free 4-[3-(2-piperidyl-ethoxy)-phenoxy]-2-amino-nitrobenzene the emulsion was worked up over ethyl acetate and after evaporating the solvent 17 g of the compound were obtained in an oily form, which could be used directly for hydrogenation.

The 4-(3-hydroxy-phenoxy)-2-amino-nitrobenzene was obtained by refluxing 190 g of 4-(3-methoxy-phenoxy)-2-amino-nitrobenzene with 10 times the amount of a 48% aqueous hydrobromic acid for 2 hours. The whole was evaporated under reduced pressure, the residue was taken up with a sodium acetate solution and the mixture was stirred for some time on the steam bath. It was suction-filtered and the crude product was purified by dissolving in ethyl acetate, filtrating with a small amount of charcoal, evaporating under reduced pressure and stirring the residue with petroleum ether. By this way 163 g of pure 4-(3-hydroxy-phenoxy)-2-amino-nitrobenzene, melting point 137° C, were obtained.

In analogous way the following compounds were prepared from the corresponding starting materials.

EXAMPLE 2

3-(2-Dimethylamino-ethoxy)-phenly-2-carbomethoxyamino-benzimidazolyl-5(6)-ether M.P. 190° Decomp.

from 4-[3-(2-dimethylamino-ethoxy)-phenoxy]-2-amino-aniline via 4-(3-hydroxy-phenoxy)-2-amino-nitrobenzene M.P. 137° and 4-[3-(2-dimethylamino-ethoxy)-phenoxy]-2-amino-nitrobenzene (oily).

EXAMPLE 3

3-(2-Diethylamino-ethoxy)-phenyl-2-carbomethoxyamino-benzimidazolyl-5(6)-ether M.P. 168° Decomp.

from 4-[3-(2-diethylamino-ethoxy)-phenoxy]-2-amino-aniline via 4-(3-hydroxy-phenoxy-2-amino-nitrobenzene M.P. 137° and 4-[3-(2-diethylamino-ethoxy)-phenoxy]-2-amino-nitrobenzene M.P. 85°.

EXAMPLE 4

3-Dimethylamino-propoxy)-phenyl-2-carbomethoxyamino-benzimidazolyl-5(6)-ether M.P. 173° Decomp.

from 4-[3-(3-dimethylamino-propoxy)-phenoxy]-2-amino-aniline via 4-(3-hydroxy-phenoxy)-2-amino-nitrobenzene M.P. 137° and 4-[3-(3-dimethylamino-propoxy)-phenoxy]-2-amino-nitrobenzene M.P. 108°.

EXAMPLE 5

4-(2-Dimethylamino-ethoxy)-phenyl-2-carbomethoxyamino-benzimidazolyl-5(6)-ether M.P, 210° Decomp.

from 4-[4-(2-dimethylamino-ethoxy)-phenoxy]-2-amino-aniline via 4-(4-hydroxy-phenoxy)-2-amino-nitrobenzene M.P. 205° and 4-[4-(2-dimethylamino-ethoxy)-phenoxy]-2-amino-nitrobenzene M.P. 125°.

Example 6

4-(2-Dimethylamino-1-methyl-ethoxy)-phenyl-2-carbomethoxyamino-benzimidazolyl-5(6)-ether M.P. 200° Decomp.

from 4-[4-(2-dimethylamino-1-methyl-ethoxy)-phenoxy]-2-amino-aniline via 4-(4-hydroxy-phenoxy)-2-amino-nitrobenzene M.P,. 205° and 4-[4-(2-dimethylamino-2-methyl-ethoxy)-phenoxy]-2-amino-nitrobenzene M.P. 125°.

EXAMPLE 7

4-(2-Diethylamino-ethoxy)-phenyl-2-carbomethoxyamino-benzimidazolyl-5(6)-ether M.P. 198° Decomp, from 4-[4-(2-diethylamino-ethoxy)-phenoxy]-2-amino-aniline via 4-(4-hydroxy-phenoxy)-2-amino-nitrobenzene M.P. 205° nd 4-[4-(2-diethylamino-ethoxy)-phenoxy]-2-amino-nitrobenzene M.P. 135°.

EXAMPLE 8

4-(2-Diisopropylamino-ethoxy)-phenyl-2-carbomethoxyaminobenzimidazolyl-5(6)-ehter M-P. 197° Decomp.

from 4-[4-(2-diisopropylamino-ethoxy)-phenoxy]-2-amino-aniline via 4-(4-hydroxy-phenoxy)-2-amino-nitrobenzene M.P. 205° and 4-[4-(2-diisopropylamino-ethoxy)-phenoxy]-2-amino-nitrobenzene M.P. 143°

EXAMPLE 9

4-(2-Piperidyl-ethoxy)-phenyl-2-carbomethoxyamino-benzimidazolyl-5(6)-ether M.P. 195° Decomp.
from 4-[4-(2-Piperidyl-ethoxy)-phenoxy]-2-amino-aniline via 4-(4-hydroxy-phenoxy)-2-amino-nitrobenzene M.P. 205°
and 4-[4-(2-piperidyl-ethoxy)-phenoxy]-2-amino-nitrobenzene M.P. 108°.

EXAMPLE 10

4-(2-Morpholyl-ethoxy)-phenyl-2-carbomethoxyamino-benzimidazolyl-5(6)-ether M.P. 200° Decomp.
from 4-[4-(2-morpholyl-ethoxy)-phenoxy]-2-amino-aniline via 4-(4-hydroxy-phenoxy)-2-amino-nitrobenzene M.P. 205°
and 4-[4-(2-morpholyl-ethoxy)-phenoxy]-2-amino-nitrobenzene M.P. 137°.

EXAMPLE 11

4-(3-Dimethylamino-propoxy)-phenyl-2-carbomethoxyaminobenzimidazolyl-5(6)-ether M.P. 182° Decomp.
from 4-[4-(3-dimethylamino-propoxy)-phenoxy]-2-amino-aniline via 4-(4-hydroxy-phenoxy)-2-amino-nitrobenzene M.P. 205°
and 4-[4-(3-dimethylamino-propoxy)-phenoxy]-2-amino-nitrobenzene M.P. 143°.

EXAMPLE 12

2-(2-Diethylamino-ethoxy)-phenyl-2-carbomethoxyamino-benzimidazolyl-5(6)-ether M.P. 197°
from 4-[2-(2-diethylamino-ethoxy)-phenoxy]-2-amino-aniline via 4-(2-hydroxy-phenoxy)-2-amino-nitrobenzene M.P. 134°
and 4-[2-(2-diethylamino-ethoxy)-phenoxy]-2-amino-nitrobenzene (oily).

EXAMPLE 13

4-(2-Diethylamino-ethoxy)-phenyl-2-carbomethoxyamino-benzimidazolyl-5(6)-thioether M.P. 163° Decomp.
from 4-[4-(2-diethylamino-ethoxy)-phenylthio]-2-amino-aniline via 4-(4-hydroxy-phenylthio)-2-amino-nitrobenzene M.P. 190°
and 4-[4-(2-diethylamino-ethoxy)-phenylthio]-2-amino-nitrobenzene resin.

EXAMPLE 14

4-(2-Diethylamino-ethoxy)-phenyl-2-carbethoxyamino-benzimidazolyl-5(6)-ether M.P. 158° Decomp.
from 4-[4-(2-diethylamino-ethoxy)-phenoxy]-2-amino-aniline via 4-(4-hydroxy-phenoxy)-2-amino-nitrobenzene M.P. 205°
and 4-[4-(2-diethylamino-ethoxy)-phenoxy]-2-amino-nitrobenzene M.P. 135°.

EXAMPLE 15

4-(2-Diethylamino-ethoxy)-phenyl-2-carbobutoxyamino-benzimidazoyl-5(6)-ether M.P. 131° Decomp.
from 4-[4-(2-diethylamino-ethoxy)-phenoxy]-2-amino-aniline via 4-(4-hydroxy-phenoxy)-2-amino-nitrobenzene M.P. 205°
and 4-[4-(2-diethylamino-ethoxy)-phenoxy]-2-amino-nitrobenzene M.P. 135°.

EXAMPLE 16

4-(2-Diethylamino-ethoxy)-phenyl-2-carbomethoxyamino-benzimidazolyl-5(6)-ketone M.P. 218° Decomp.
from 4-[4-(2-diethylamino-ethoxy)-benzoyl]-2-amino-aniline via 5-(4-hydroxy-benzoyl)-2-amino-nitrobenzene M.P. 220°
and 5-[4-(2-diethylamino-ethoxy)-benzoyl]-2-amino-nitrobenzene M.P. 93°.

The temperatures are by degrees Celcius.

EXAMPLE 17

(Process b)

To a solution of 4.2 g of cyanamide in 20 ml of water 9.0 g of chloroformic acid methyl ester and 21.8 g of 33% sodium hydroxide solution were added. Stirring was continued for one and a half hour, while the temperature was maintained between 30 and 35° C. Then a solution of 26.5 g of 4-[3-(2-piperidylethoxy)-phenoxy]-2-amino-aniline dissolved in 200 ml isopropanol was added and the temperature was increased to 80° C. After addition of 20 ml of glacial acetic acid the reaction mixture was maintained for 3 – 4 hours at 90° C. The hot solution was mixed dropwise with concentrated ammonia until the reaction became alkaline, whereby a thick slurry was separated.

The liquid was separated and the crude product was purified by dissolution in a mixture of 400 ml of methanol and 35 ml of a 2N hydrochloric acid at 50° C, filtration with charcoal and another precipitation with ammonia. The pure 3-(2-piperidyl-ethoxy)-phenyl-2-carbomethoxyamino-benzimidazolyl-5(6)-ether was suction-filtered and washed out with methanol and then with water. Yield: 22 g having a decomposition point of 200° C. The reaction product was identical with the product obtained in Example 1. The 4-[3-(2-piperidyl-ethoxy)-phenoxy]-2-amino-aniline was obtained according to Example 1 from 4-(3-methoxyphenoxy)-2-amino-nitrobenzene via the intermediate stages also described in Example 1.

In analogous manner the following compounds were prepared from the corresponding starting materials:

EXAMPLE 18

3-(2-Dimethylamino-ethoxy)-phenyl-2-carbomethoxyamino-benzimidazolyl-5(6)-ether M.P. 190° C decomp.
from 4-[3-(2-dimethylamino-ethoxy)-phenoxy]-2-amino-aniline via 4-(3-hydroxy-phenoxy)-2-amino-nitrobenzene M.P. 137° C
and 4-[3-(2-dimethylamino-ethoxy)-phenoxy]-2-amino-nitrobenzene (oily).

EXAMPLE 19

3-(Dimethylamino-propoxy)-phenyl-2-carbomethoxyamino-benzimidazolyl-5(6)-ether M.P. 173° C decomp.
from 4-[3-(3-dimethylamino-propoxy)-phenoxy]-2-amino-aniline via 4-(3-hydroxy-phenoxy)-2-amino-nitrobenzene M.P. 137° C
and 4-[3-(3-dimethylamino-propoxy-phenoxy]-2-amino-nitrobenzene M.P. 108° C.

EXAMPLE 20

4-(2-Dimethylamino-ethoxy)-phenyl-2-carbomethoxyamino-benzimidazolyl-5(6)-ether M.P. 210° C decomp.
from 4-[4-(2-dimethylamino-ethoxy)-phenoxy]-2-amino aniline via 4-(4-hydroxy-phenoxy)-2-amino-nitrobenzene M.P. 205° C
and 4-[4-(2-dimethylamino-ethoxy)-phenoxy]-2-amino-nitrobenzene M.P. 125° C

EXAMPLE 21

4-(2-Diethylamino-ethoxy)-phenyl-2-carbomethoxyamino-benzimidazolyl-5(6)-ether M.P. 198° C decomp.
from 4-[4-(2-diethylamino-ethoxy)-phenoxy]-2-amino-aniline via 4-(4-hydroxy-phenoxy)-2-amino-nitrobenzene M.P. 205° C and 4-[4-(2-diethylamino-ethoxy)-phenoxy]-2-amino-nitrobenzene M.P. 135° C

EXAMPLE 22

4-(2-Piperidyl-ethoxy)-phenyl-2-carbomethoxyamino-benzimidazolyl-5(6)-ether M.P. 195° C decomp.
from 4-[4-(2-piperidyl-ethoxy)-phenoxy]-2-amino-aniline via 4-(4-hydroxy-phenoxy)-2-amino-nitrobenzene M.P. 205° C
and 4-[4-(2-piperidyl-ethoxy)-phenoxy]-2-amino-nitrobenzene M.P. 108° C

EXAMPLE 23

4-(2-Diethylamino-ethoxy)-phenyl-2-carbomethoxyamino-benzimidazolyl-5(6)-thioether M.P. 163° C decomp.
from 4-[4-(2-diethylamino-ethoxy)-phenylthio]-2-amino-aniline via 4-(4-hydroxy-phenylthio)-2-amino-nitrobenzene M.P. 190° C and 4-[4-(2-diethylamino-ethoxy)-phenylthio]-2-amino-nitrobenzene, resin

EXAMPLE 24

4-(2-Diethylamino-ethoxy)-phenyl-2-carbomethoxyamino-benzimidazolyl-5(6)-ketone M.P. 218° C decomp.
from 4-[4-(2-diethylamino-ethoxy)-benzoyl]-2-amino-aniline via 5-(4-hydroxy-benzoyl)-2-amino-nitrobenzene M.P. 220° C
and 5-[4-(2-diethylamino-ethoxy)-benzoyl]-2-amino-nitrobenzene M.P. 93° C.

EXAMPLE 25

(Process c)

17.9 g of bis-methylthio-methylenamino-formic acid methyl ester were added to 32.7 g of 4-[3-(2-piperidyl-ethoxy)-phenoxy]-2-amino-aniline in 300 ml of tetrahydrofurane and the mixture was refluxed for some hours. It was diluted with water and by dropwise addition of ammonia the reaction mixture was adjusted to an alkaline range. The liquid was suction-filtered and the crude product was purified as described in Example 1 by reprecipitation in methanolic solution. Yield: 20 g having a decomposition point of 200° C. The reaction product was identical with the product described in Example 1. The 4-(3-(2-piperidyl-ethoxy)-phenoxy)-2-amino-aniline was obtained according to Example 1 from 4-(3-methoxy-phenoxy)-2-amino-nitrobenzene via the intermediate stages also described in Example 1.

EXAMPLE 26:

To a cooled solution of 19.7 g of imino-dithio-carbonic acid methyl ester hydrochloride and 12.5 g of chloroformic acid methyl ester in 50 ml of water, 10% sodium hydroxide solution was added dropwise, while the temperature should not exceed 10° C. As soon as the pH-value was adjusted to 7.5, 32.7 g of 4-[3-(2-piperidyl-ethoxy)-phenoxy]-2-amino-aniline in 100 ml of glacial acetic acid were added, the mixture was refluxed for 2 hours, and care was taken that a medium of acetic acid was maintained. The mixture was diluted with water and made alkaline by dropwise addition of concentrated ammonia. After cooling the 3-(2-piperidyl-ethoxy)-phenyl-2-carbomethoxyamino-benzimidazolyl-5(6)-ether was filtered and purified as described in Example 1. The properties thereof were identical to those of the reaction product described in Example 1.

EXAMPLE 27

3-(2-Dimethylamino-ethoxy)-phenyl-2-carbomethoxyamino-benzimidazolyl-5(6)-ether M.P. 190° C decomp.
from 4-[3-(2-dimethylamino-ethoxy)-phenoxy]-2-amino-aniline via 4-(3-hydroxy-phenoxy)-2-amino-nitrobenzene M.P. 137° C
and 4-[3-(2-dimethylamino-ethoxy)-phenoxy]-2-amino-nitrobenzene (oily)

EXAMPLE 28

3-(Dimethyl-propoxy)-phenyl-2-carbomethoxyamino-benzimidazolyl-5(6)-ether M.P. 173° C decomp.
from 4-[3-(3-dimethylamino-propoxy)-phenoxy]-2-amino-aniline via 4-(3-hydroxy-phenoxy)-2-amino-nitrobenzene M.P. 137° C
and 4-[3-(3-dimethylamino-propoxy)-phenoxy]-2-amino-nitrobenbenzene M.P. 108° C

EXAMPLE 29

4-(2-Dimethylamino-ethoxy)-phenyl-2-carbomethoxyamino-benzimidazolyl-5(6)-ether M.P. 210° C decomp.
from 4-[4-(2-dimethylamino-ethoxy)-phenoxy]-2-amino-aniline via 4-(4-hydroxyl-phenoxy)-2-amino-nitrobenzene M.P. 205° C
and 4-[4-(2-dimethylamino-ethoxy)-phenoxy]-2-amino-nitrobenzene M.P. 125° C

EXAMPLE 30

4-(2-Diethylamino-ethoxy)-phenyl-2-carbomethoxyamino-benzimidazolyl-5(6)-ether M.P. 198° C decomp.
from 4-[4-(2-diethylamino-ethoxy)-phenoxy]-2-amino-aniline via 4-(4-hydroxy-phenoxy)-2-amino-nitrobenzene M.P. 205° C
and 4-[4-(2-diethylamino-ethoxy)-phenoxy]-2-amino-nitrobenzene M.P. 135° C.

EXAMPLE 31

4-(2-Piperidyl-ethoxy)-phenyl-2-carbomethoxyamino-benzimidazolyl-5(6)-ether M.P. 195° C decomp.
from 4-[4-(2-piperidyl-ethoxy)-phenoxy]-2-amino-aniline via 4-(4-hydroxy-phenoxy)-2-amino-nitrobenzene M.P. 205° C and 4-[4-(2-piperidyl-ethoxy)-phenoxy]-2-amino-nitrobenzene M.P. 108° C.

EXAMPLE 32

4-(2-Diethylamino-ethoxy)-phenyl-2-carbomethoxyamino-benzimidazolyl-5(6)-thioether M.P. 163° C decomp.
from 4-[4-(2-dimethylaminoethoxy)-phenylthio]-2-amino-aniline via 4-(4-hydroxy-phenylthio)-2-amino-nitrobenzene M.P. 190° C
and 4-[4-(2-diethylamino-ethoxy)-phenylthio]-2-amino-nitrobenzene; resin

EXAMPLE 33

4-(2-Diethylamino-ethoxy)-phenyl-2-carbomethoxyamino-benzimidazolyl-5(6)-ketone M.P. 218° C decomp. from 4-[4-(2-diethylamino-ethoxy)-benzoyl]-2-amino-aniline via 5-(4-hydroxy-benzoyl)-2-amino-nitrobenzene M.P. 220° c and 5-[4-(2-diethylamino-ethoxy)-benzoyl]-2-amino-nitrobenzene M.P. 93° C.

What we claim is:
1. A basically substituted 2-carbalkoxyamino-benzimidazoly 5-(6)-phenyl ether or -ketone of the formula

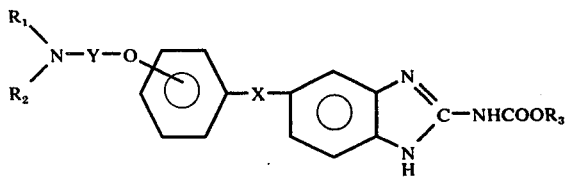

wherein $R_3$ is alkyl having 1 to 4 carbon atoms, X is oxygen, sulfur or

Y is a straight-chained or branched alkylene of 1 to 4 carbon atoms and $R_1$ and $R_2$ represent alkyl having 1 to 4 carbon atoms, whereby $R_1$ and $R_2$ together with the supporting nitrogen atom may also represent pyrrolidine, piperidine, morpholine or thiomorpholine, and a salt thereof with a physiologically tolerable acid.

2. A compound as defined in claim 1, wherein $R_3$ is methyl, x is oxygen, sulfur or

Y is —(CH$_2$)$_2$— or —(CH$_2$)$_3$— and $R_1$ and $R_2$ are methyl or ethyl or together with the nitrogen atom carrying them the piperidine ring.

3. The compound as claimed in claim 1 which is 3-(2-piperidyl-ethoxy)-phenyl-2-carbomethoxyamino-benzimidazolyl-5(6)-ether.

4. The compound as claimed in claim 1 which is 3-(2-dimethyl-amino-ethoxy)-phenyl-2-carbomethoxyamino-benzimidazolyl-5(6)-ether.

5. The compound as claimed in claim 1 which is 3-(dimethylamino-propoxy)-phenyl-2-carbomethoxyamino-benzimidazolyl5(6)-ether.

6. The compound as claimed in claim 1 which is 4-(2-dimethyl-amino-ethoxy)-phenyl-2-carbomethoxyamino-benzimidazolyl-5(6)-ether.

7. The compound as claimed in claim 1 which is 4-(2-diethylamino-ethoxy)-phenyl-2-carbomethoxyamino-benzimidazolyl-5(6)-ether.

8. The compound as claimed in claim 1 which is 4-(2-piperidyl-ethoxy)-phenyl-2-carbomethoxyamino-benzimidazolyl-5(6)-ether.

9. The compound as claimed in claim 1 which is 4-(2-diethylamino-ethoxy)-phenyl-2-carbomethoxyamino-benzimidazolyl-5(6)-thio ether.

10. The compound as claimed in claim 1 which is 4-(2-diethylamino-ethoxy)-phenyl-2-carbomethoxyamino-benzimidazolyl-5(6)-ketone.

11. Anthelmintic composition containing as the active ingredient an effective amount of a compound as claimed in claim 1 in admixture with a pharmaceutically acceptable carrier.

12. Method of combatting helminths which comprises administering an effective amount of a compound as claimed in claim 1 to the infected organism.

* * * * *